(12) United States Patent
Cartledge et al.

(10) Patent No.: US 9,827,125 B2
(45) Date of Patent: *Nov. 28, 2017

(54) SEALABLE ENDOVASCULAR IMPLANTS AND METHODS FOR THEIR USE

(71) Applicant: Edwards Lifesciences CardiAQ LLC, Irvine, CA (US)

(72) Inventors: Richard George Cartledge, Boca Raton, FL (US); John P. Cartledge, Boca Raton, FL (US)

(73) Assignee: Edwards Lifesciences CardiAQ LLC, Irvine, CA (US)

( * ) Notice: Subject to any disclaimer, the term of this patent is extended or adjusted under 35 U.S.C. 154(b) by 113 days.

This patent is subject to a terminal disclaimer.

(21) Appl. No.: 14/735,982

(22) Filed: Jun. 10, 2015

(65) Prior Publication Data

US 2015/0272756 A1 Oct. 1, 2015

Related U.S. Application Data

(62) Division of application No. 13/544,379, filed on Jul. 9, 2012, now Pat. No. 9,138,335, which is a division
(Continued)

(51) Int. Cl.
*A61F 2/06* (2013.01)
*A61F 2/954* (2013.01)
(Continued)

(52) U.S. Cl.
CPC ............ *A61F 2/954* (2013.01); *A61F 2/07* (2013.01); *A61F 2/856* (2013.01); *A61F 2/06* (2013.01);
(Continued)

(58) Field of Classification Search
CPC ...... A61F 2/06; A61F 2/07; A61F 2/95; A61F 2002/9534; A61F 2002/9528
See application file for complete search history.

(56) References Cited

U.S. PATENT DOCUMENTS

| 2,684,069 A | 7/1954 | Donaldson et al. |
| 3,490,975 A | 1/1970 | Lightwood et al. |

(Continued)

FOREIGN PATENT DOCUMENTS

| CA | 2557657 A1 | 9/2005 |
| CN | 1684644 A | 10/2005 |

(Continued)

OTHER PUBLICATIONS

Official Communication From the European Patent Office for European Pat. App. No. 12841445.5 dated Feb. 18, 2016.
(Continued)

*Primary Examiner* — Diane Yabut
(74) *Attorney, Agent, or Firm* — Klarquist Sparkman, LLP; AnneMarie Kaiser

(57) ABSTRACT

A sealable vascular endograft system for placement in a vascular defect includes a delivery catheter shaped to be disposed within a blood vessel. The delivery catheter includes an implant delivery catheter sheath defining an implant delivery catheter lumen and an endovascular implant removably disposed within the implant delivery catheter lumen in a compressed or folded state for delivery thereof to the vascular defect. The endovascular implant includes a tubular implant body and a sealable circumferential collar including a variable sealing device and a control lead traversing from the variable sealing device to a user and controlling variability of the variable sealing device by the user. The sealing device and the control lead cooperate to reversibly expand and contract the sealable circumferential collar to circumferentially adjust during deployment thereof to achieve a repositionable fluid-tight seal between the sealable circumferential collar and the internal walls proximal to the vascular defect.

17 Claims, 27 Drawing Sheets

Related U.S. Application Data of application No. 11/888,009, filed on Jul. 31, 2007, now Pat. No. 8,252,036.

(60) Provisional application No. 60/834,627, filed on Aug. 1, 2006, provisional application No. 60/834,401, filed on Jul. 31, 2006.

(51) Int. Cl.
*A61F 2/07* (2013.01)
*A61F 2/856* (2013.01)
*A61F 2/95* (2013.01)
*A61F 2/94* (2013.01)
*A61F 2/90* (2013.01)

(52) U.S. Cl.
CPC . *A61F 2/90* (2013.01); *A61F 2/94* (2013.01); *A61F 2/95* (2013.01); *A61F 2002/067* (2013.01); *A61F 2002/075* (2013.01); *A61F 2002/077* (2013.01); *A61F 2002/9511* (2013.01); *A61F 2002/9528* (2013.01); *A61F 2002/9534* (2013.01); *A61F 2250/006* (2013.01); *A61F 2250/0018* (2013.01); *A61F 2250/0039* (2013.01); *A61F 2250/0065* (2013.01); *A61F 2250/0069* (2013.01)

(56) References Cited

U.S. PATENT DOCUMENTS

| | | |
|---|---|---|
| 3,657,744 A | 4/1972 | Ersek |
| 3,667,474 A | 6/1972 | Lapkin et al. |
| 4,056,854 A | 11/1977 | Boretos et al. |
| 4,323,525 A | 4/1982 | Bornat |
| 4,459,252 A | 7/1984 | MacGregor et al. |
| 4,475,972 A | 10/1984 | Wong et al. |
| 4,585,000 A | 4/1986 | Hershenson et al. |
| 4,602,911 A | 7/1986 | Ahmadi |
| 4,655,771 A | 4/1987 | Wallsten |
| 4,800,882 A | 1/1989 | Gianturco et al. |
| 4,851,009 A | 7/1989 | Pinchuk et al. |
| 4,906,244 A | 3/1990 | Pinchuk et al. |
| 4,921,484 A | 5/1990 | Hillstead |
| 4,954,126 A | 9/1990 | Wallsten |
| 4,990,151 A | 2/1991 | Wallsten et al. |
| 5,019,090 A | 5/1991 | Pinchuk |
| 5,061,275 A | 10/1991 | Wallsten et al. |
| 5,092,877 A | 3/1992 | Pinchuk et al. |
| 5,133,742 A | 7/1992 | Pinchuk et al. |
| 5,163,951 A | 11/1992 | Pinchuk et al. |
| 5,180,368 A | 1/1993 | Garrison |
| 5,211,658 A | 5/1993 | Clouse et al. |
| 5,229,431 A | 7/1993 | Pinchuk et al. |
| 5,411,552 A | 5/1995 | Andersen et al. |
| 5,425,705 A | 6/1995 | Evard et al. |
| 5,441,516 A | 8/1995 | Wang et al. |
| 5,443,477 A | 8/1995 | Marin et al. |
| 5,449,372 A | 9/1995 | Schmaltz et al. |
| 5,456,667 A | 10/1995 | Ham et al. |
| 5,456,694 A | 10/1995 | Marin |
| 5,484,565 A | 1/1996 | Larsen et al. |
| 5,531,785 A | 7/1996 | Love et al. |
| 5,536,251 A | 7/1996 | Evard et al. |
| 5,554,183 A | 9/1996 | Nazari |
| 5,562,725 A | 10/1996 | Schmitt et al. |
| 5,569,296 A | 10/1996 | Marin et al. |
| 5,575,818 A | 11/1996 | Pinchuk et al. |
| 5,591,196 A | 1/1997 | Marin et al. |
| 5,593,417 A | 1/1997 | Rhodes et al. |
| 5,617,878 A | 4/1997 | Taheri |
| 5,618,300 A | 4/1997 | Marin et al. |
| 5,628,788 A | 5/1997 | Pinchuk et al. |
| 5,632,772 A | 5/1997 | Alcime et al. |
| 5,639,278 A | 6/1997 | Dereume et al. |
| 5,641,373 A | 6/1997 | Shannon et al. |
| 5,693,088 A | 12/1997 | Lazarus et al. |
| 5,697,948 A | 12/1997 | Marin et al. |
| 5,700,269 A | 12/1997 | Pinchuk et al. |
| 5,700,285 A | 12/1997 | Myers et al. |
| 5,713,907 A | 2/1998 | Hogendijk et al. |
| 5,713,948 A | 2/1998 | Uflacker |
| 5,718,159 A | 2/1998 | Thompson |
| 5,718,973 A | 2/1998 | Lewis et al. |
| 5,720,776 A | 2/1998 | Chuter et al. |
| 5,723,004 A | 3/1998 | Dereume et al. |
| 5,725,547 A | 3/1998 | Chuter |
| 5,735,892 A | 4/1998 | Myers et al. |
| 5,776,186 A | 7/1998 | Uflacker |
| 5,797,951 A | 8/1998 | Mueller |
| 5,810,870 A | 9/1998 | Myers et al. |
| 5,824,034 A | 10/1998 | Schmitt et al. |
| 5,824,037 A | 10/1998 | Fogarty et al. |
| 5,824,040 A | 10/1998 | Cox et al. |
| 5,840,081 A | 11/1998 | Andersen et al. |
| 5,843,173 A | 12/1998 | Shannon et al. |
| 5,855,565 A | 1/1999 | Bar-Cohen |
| 5,855,598 A | 1/1999 | Pinchuk et al. |
| 5,871,536 A | 2/1999 | Lazarus et al. |
| 5,925,075 A | 7/1999 | Myers et al. |
| 5,928,258 A | 7/1999 | Khan et al. |
| 5,948,018 A | 9/1999 | Dereume et al. |
| 5,957,949 A | 9/1999 | Leonhardt et al. |
| 5,968,091 A | 10/1999 | Pinchuk et al. |
| 5,972,029 A | 10/1999 | Fuisz |
| 5,976,650 A | 11/1999 | Campbell et al. |
| 5,993,482 A | 11/1999 | Chuter |
| 5,993,489 A | 11/1999 | Lewis et al. |
| 6,015,431 A | 1/2000 | Thornton et al. |
| 6,027,529 A | 2/2000 | Roychowdhury et al. |
| 6,027,811 A | 2/2000 | Campbell et al. |
| 6,036,716 A | 3/2000 | Kruchinin et al. |
| 6,110,198 A | 8/2000 | Fogarty et al. |
| 6,120,534 A | 9/2000 | Ruiz et al. |
| 6,123,722 A | 9/2000 | Fogarty et al. |
| 6,123,723 A | 9/2000 | Konya et al. |
| 6,126,685 A | 10/2000 | Lenker et al. |
| 6,129,756 A | 10/2000 | Kugler et al. |
| 6,159,565 A | 12/2000 | Campbell et al. |
| 6,165,212 A | 12/2000 | Dereume et al. |
| 6,168,614 B1 | 1/2001 | Andersen et al. |
| 6,168,616 B1 | 1/2001 | Brown, III |
| 6,168,621 B1 | 1/2001 | Vrba |
| 6,193,745 B1 | 2/2001 | Fogarty et al. |
| 6,217,585 B1 | 4/2001 | Houser et al. |
| 6,221,102 B1 | 4/2001 | Baker et al. |
| 6,224,626 B1 | 5/2001 | Steinke |
| 6,267,783 B1 | 7/2001 | Letendre et al. |
| 6,267,834 B1 | 7/2001 | Shannon et al. |
| 6,273,895 B1 | 8/2001 | Pinchuk et al. |
| 6,276,661 B1 | 8/2001 | Laird |
| 6,283,991 B1 | 9/2001 | Cox et al. |
| 6,295,940 B1 | 10/2001 | Shonteff |
| 6,296,661 B1 | 10/2001 | Davila et al. |
| 6,299,636 B1 | 10/2001 | Schmitt et al. |
| 6,299,637 B1 | 10/2001 | Shaolian et al. |
| 6,309,413 B1 | 10/2001 | Dereume et al. |
| 6,312,458 B1 | 11/2001 | Golds |
| 6,312,460 B2 | 11/2001 | Drasler et al. |
| 6,312,465 B1 | 11/2001 | Griffin et al. |
| 6,319,276 B1 | 11/2001 | Holman et al. |
| 6,327,772 B1 | 12/2001 | Zadno-Azizi |
| 6,344,052 B1 | 2/2002 | Greenan et al. |
| 6,348,061 B1 | 2/2002 | Whitman |
| 6,348,066 B1 | 2/2002 | Pinchuk et al. |
| 6,355,030 B1 | 3/2002 | Aldrich et al. |
| 6,355,055 B1 | 3/2002 | Waksman et al. |
| 6,357,104 B1 | 3/2002 | Myers |
| 6,402,779 B1 | 6/2002 | Colone et al. |
| 6,425,916 B1 | 7/2002 | Garrison et al. |
| 6,451,052 B1 | 9/2002 | Burmeister et al. |
| 6,454,795 B1 | 9/2002 | Chuter |
| 6,458,092 B1 | 10/2002 | Gambale et al. |
| 6,461,327 B1 | 10/2002 | Addis et al. |
| 6,464,720 B2 | 10/2002 | Boatman et al. |

(56) References Cited

U.S. PATENT DOCUMENTS

| | | |
|---|---|---|
| 6,488,705 B2 | 12/2002 | Schmitt et al. |
| 6,497,724 B1 | 12/2002 | Stevens et al. |
| 6,520,988 B1 | 2/2003 | Colombo et al. |
| 6,530,952 B2 | 3/2003 | Vesely |
| 6,540,782 B1 | 4/2003 | Snyders |
| 6,547,815 B2 | 4/2003 | Myers |
| 6,558,396 B1 | 5/2003 | Inoue |
| 6,569,191 B1 | 5/2003 | Hogan |
| 6,569,196 B1 | 5/2003 | Vesely |
| 6,575,994 B1 | 6/2003 | Marin et al. |
| 6,579,297 B2 | 6/2003 | Bicek et al. |
| 6,582,458 B1 | 6/2003 | White et al. |
| 6,582,462 B1 | 6/2003 | Andersen et al. |
| 6,648,913 B1 | 11/2003 | Yee et al. |
| 6,656,215 B1 | 12/2003 | Yanez et al. |
| 6,669,720 B1 | 12/2003 | Pierce |
| 6,673,103 B1 | 1/2004 | Golds et al. |
| 6,682,558 B2 | 1/2004 | Tu et al. |
| 6,695,813 B1 | 2/2004 | Boyle et al. |
| 6,716,230 B2 | 4/2004 | Whitman |
| 6,719,782 B1 | 4/2004 | Chuter |
| 6,730,118 B2 | 5/2004 | Spenser et al. |
| 6,730,121 B2 | 5/2004 | Ortiz et al. |
| 6,733,521 B2 | 5/2004 | Chobotov et al. |
| 6,733,525 B2 | 5/2004 | Yang et al. |
| 6,740,105 B2 | 5/2004 | Yodfat et al. |
| 6,761,733 B2 | 7/2004 | Chobotov et al. |
| 6,773,456 B1 | 8/2004 | Gordon et al. |
| 6,814,748 B1 | 11/2004 | Baker et al. |
| 6,837,893 B2 | 1/2005 | Miller |
| 6,860,900 B2 | 3/2005 | Clerc et al. |
| 6,860,901 B1 | 3/2005 | Baker et al. |
| 6,863,686 B2 | 3/2005 | Shannon |
| 6,875,231 B2 | 4/2005 | Anduiza et al. |
| 6,881,221 B2 | 4/2005 | Golds |
| 6,890,350 B1 | 5/2005 | Walak |
| 6,893,459 B1 | 5/2005 | Macoviak |
| 6,893,460 B2 | 5/2005 | Spenser et al. |
| 6,908,478 B2 | 6/2005 | Alferness et al. |
| 6,918,926 B2 | 7/2005 | Letort |
| 6,929,659 B2 | 8/2005 | Pinchuk |
| 6,945,994 B2 | 9/2005 | Austin et al. |
| 6,949,119 B2 | 9/2005 | Myers |
| 6,951,571 B1 | 10/2005 | Srivastava |
| 6,994,722 B2 | 2/2006 | DiCarlo |
| 7,004,176 B2 | 2/2006 | Lau |
| 7,007,396 B2 | 3/2006 | Rudko et al. |
| 7,011,681 B2 | 3/2006 | Vesely |
| 7,018,400 B2 | 3/2006 | Lashinski et al. |
| 7,033,389 B2 | 4/2006 | Sherry |
| 7,041,132 B2 | 5/2006 | Quijano et al. |
| 7,052,511 B2 | 5/2006 | Weldon et al. |
| 7,090,688 B2 | 8/2006 | Nishtala et al. |
| 7,097,658 B2 | 8/2006 | Oktay |
| 7,112,217 B1 | 9/2006 | Kugler et al. |
| 7,122,051 B1 | 10/2006 | Dallara et al. |
| 7,137,993 B2 | 11/2006 | Acosta et al. |
| 7,141,063 B2 | 11/2006 | White |
| 7,152,605 B2 | 12/2006 | Khairkhahan et al. |
| 7,160,318 B2 | 1/2007 | Greenberg et al. |
| 7,166,125 B1 | 1/2007 | Baker et al. |
| 7,169,172 B2 | 1/2007 | Levine et al. |
| 7,175,656 B2 | 2/2007 | Khairkhahan |
| 7,217,287 B2 | 5/2007 | Wilson et al. |
| 7,235,093 B2 | 6/2007 | Gregorich |
| 7,250,028 B2 | 7/2007 | Julian et al. |
| 7,258,696 B2 | 8/2007 | Rabkin et al. |
| 7,297,150 B2 | 11/2007 | Cartledge et al. |
| 7,326,236 B2 | 2/2008 | Andreas et al. |
| 7,329,279 B2 | 2/2008 | Haug et al. |
| 7,331,991 B2 | 2/2008 | Kheradvar et al. |
| 7,374,571 B2 | 5/2008 | Pease et al. |
| 7,381,219 B2 | 6/2008 | Salahieh et al. |
| 7,393,360 B2 | 7/2008 | Spenser et al. |
| 7,399,315 B2 | 7/2008 | Iobbi |
| 7,435,257 B2 | 10/2008 | Lashinski et al. |
| 7,445,630 B2 | 11/2008 | Lashinski et al. |
| 7,452,371 B2 | 11/2008 | Pavcnik et al. |
| 7,455,690 B2 | 11/2008 | Cartledge et al. |
| 7,481,836 B2 | 1/2009 | Greenan |
| 7,507,252 B2 | 3/2009 | Lashinski et al. |
| 7,510,572 B2 | 3/2009 | Gabbay |
| 7,524,331 B2 | 4/2009 | Birdsall |
| 7,544,206 B2 | 6/2009 | Cohn |
| 7,556,646 B2 | 7/2009 | Yang et al. |
| 7,591,848 B2 | 9/2009 | Allen |
| 7,597,704 B2 | 10/2009 | Frazier et al. |
| 7,625,403 B2 | 12/2009 | Krivoruchko |
| 7,637,935 B2 | 12/2009 | Pappas et al. |
| 7,674,296 B2 | 3/2010 | Rhoda et al. |
| 7,682,390 B2 | 3/2010 | Seguin |
| 7,691,141 B2 | 4/2010 | Lewis et al. |
| 7,708,773 B2 | 5/2010 | Pinchuk et al. |
| 7,713,282 B2 | 5/2010 | Frazier et al. |
| 7,722,662 B2 | 5/2010 | Steinke et al. |
| 7,727,270 B2 | 6/2010 | Rucker |
| 7,763,065 B2 | 7/2010 | Schmid |
| 7,780,724 B2 | 8/2010 | Kheradvar et al. |
| 7,785,341 B2 | 8/2010 | Forster et al. |
| 7,803,185 B2 | 9/2010 | Gabbay |
| 7,806,917 B2 | 10/2010 | Xiao |
| 7,828,839 B2 | 11/2010 | Cook et al. |
| 7,862,577 B2 | 1/2011 | Gray et al. |
| 7,862,609 B2 | 1/2011 | Butaric et al. |
| 7,887,583 B2 | 2/2011 | Macoviak |
| 7,896,913 B2 | 3/2011 | Damm et al. |
| 7,914,574 B2 | 3/2011 | Schmid |
| 7,935,141 B2 | 5/2011 | Randall et al. |
| 7,947,071 B2 | 5/2011 | Schmid |
| 7,959,666 B2 | 6/2011 | Salahieh et al. |
| 7,972,370 B2 | 7/2011 | Douk et al. |
| 7,988,724 B2 | 8/2011 | Salahieh et al. |
| 7,998,189 B2 | 8/2011 | Kölbel et al. |
| 8,012,197 B2 | 9/2011 | Bashiri et al. |
| 8,016,873 B1 | 9/2011 | Drasler et al. |
| 8,021,421 B2 | 9/2011 | Fogarty et al. |
| 8,043,356 B2 | 10/2011 | Kölbel et al. |
| 8,043,357 B2 | 10/2011 | Hartley |
| 8,048,153 B2 | 11/2011 | Salahieh et al. |
| 8,052,732 B2 | 11/2011 | Mitchell et al. |
| 8,052,749 B2 | 11/2011 | Salahieh et al. |
| 8,052,750 B2 | 11/2011 | Tuval et al. |
| 8,062,344 B2 | 11/2011 | Dorn et al. |
| 8,062,345 B2 | 11/2011 | Ouellette et al. |
| 8,128,681 B2 | 3/2012 | Shoemaker et al. |
| 8,157,853 B2 | 4/2012 | Laske et al. |
| 8,157,860 B2 | 4/2012 | McNamara et al. |
| 8,226,707 B2 | 7/2012 | White |
| 8,252,036 B2 * | 8/2012 | Cartledge ............ A61F 2/07 623/1.11 |
| 8,500,790 B2 | 8/2013 | Khairkhahan |
| 8,523,936 B2 | 9/2013 | Schmid |
| 8,540,762 B2 | 9/2013 | Schmid |
| 8,647,378 B2 | 2/2014 | Mews |
| 8,673,001 B2 | 3/2014 | Cartledge |
| 8,685,080 B2 | 4/2014 | White |
| 8,852,261 B2 | 10/2014 | White |
| 8,858,620 B2 | 10/2014 | Salahieh |
| 8,894,703 B2 | 11/2014 | Salahieh |
| 8,998,976 B2 | 4/2015 | Gregg |
| 2001/0023369 A1 | 9/2001 | Chobotov |
| 2001/0025161 A1 | 9/2001 | Martinez |
| 2001/0053931 A1 | 12/2001 | Hess et al. |
| 2002/0032481 A1 | 3/2002 | Gabbay |
| 2002/0055768 A1 | 5/2002 | Hess et al. |
| 2002/0077695 A1 | 6/2002 | Swanson et al. |
| 2002/0120327 A1 | 8/2002 | Cox et al. |
| 2003/0004560 A1 | 1/2003 | Chobotov et al. |
| 2003/0009211 A1 | 1/2003 | DiCarlo |
| 2003/0040791 A1 | 2/2003 | Oktay |
| 2003/0050694 A1 | 3/2003 | Yang et al. |
| 2003/0055495 A1 | 3/2003 | Pease |
| 2003/0074048 A1 | 4/2003 | Sherry |
| 2003/0105516 A1 | 6/2003 | Austin |

(56) References Cited

U.S. PATENT DOCUMENTS

| | | |
|---|---|---|
| 2003/0120331 A1 | 6/2003 | Chobotov |
| 2003/0135268 A1 | 7/2003 | Desai |
| 2003/0176911 A1 | 9/2003 | Iancea |
| 2003/0191518 A1 | 10/2003 | Spiridigliozzi et al. |
| 2003/0199967 A1 | 10/2003 | Hartley et al. |
| 2003/0204249 A1 | 10/2003 | Letort |
| 2003/0216770 A1 | 11/2003 | Persidsky et al. |
| 2003/0229389 A1 | 12/2003 | Escano |
| 2004/0049266 A1 | 3/2004 | Anduiza et al. |
| 2004/0138734 A1 | 7/2004 | Chobotov et al. |
| 2004/0148021 A1 | 7/2004 | Cartledge |
| 2004/0162603 A1 | 8/2004 | Golds et al. |
| 2004/0230289 A1 | 11/2004 | DiMatteo et al. |
| 2004/0243221 A1 | 12/2004 | Fawzi |
| 2005/0002981 A1 | 1/2005 | Lahtinen et al. |
| 2005/0038497 A1 | 2/2005 | Neuendorf et al. |
| 2005/0055089 A1 | 3/2005 | Macoviak et al. |
| 2005/0075712 A1 | 4/2005 | Biancucci et al. |
| 2005/0075725 A1 | 4/2005 | Rowe |
| 2005/0096737 A1 | 5/2005 | Shannon et al. |
| 2005/0137686 A1 | 6/2005 | Salahieh et al. |
| 2005/0137699 A1 | 6/2005 | Salahieh |
| 2005/0171599 A1 | 8/2005 | White |
| 2005/0228484 A1 | 10/2005 | Stephens et al. |
| 2006/0009833 A1 | 1/2006 | Chobotov |
| 2006/0030927 A1 | 2/2006 | Hess |
| 2006/0064151 A1 | 3/2006 | Guterman |
| 2006/0074482 A1 | 4/2006 | Lewis et al. |
| 2006/0089708 A1 | 4/2006 | Osse et al. |
| 2006/0135984 A1 | 6/2006 | Kramer et al. |
| 2006/0149350 A1 | 7/2006 | Patel et al. |
| 2006/0161247 A1 | 7/2006 | Sherry |
| 2006/0173527 A1 | 8/2006 | Scherrible |
| 2006/0212113 A1 | 9/2006 | Shaolian et al. |
| 2006/0217796 A1 | 9/2006 | DiMatteo et al. |
| 2006/0253190 A1 | 11/2006 | Kuo |
| 2007/0010876 A1 | 1/2007 | Salahieh |
| 2007/0010877 A1 | 1/2007 | Salahieh |
| 2007/0088431 A1 | 4/2007 | Bourang et al. |
| 2007/0088436 A1 | 4/2007 | Parsons et al. |
| 2007/0100427 A1 | 5/2007 | Perouse |
| 2007/0106364 A1 | 5/2007 | Buzzard et al. |
| 2007/0123972 A1 | 5/2007 | Greenberg et al. |
| 2007/0142906 A1 | 6/2007 | Figulla |
| 2007/0142907 A1 | 6/2007 | Moaddeb et al. |
| 2007/0179591 A1 | 8/2007 | Baker et al. |
| 2007/0208223 A1 | 9/2007 | Julian et al. |
| 2007/0225797 A1 | 9/2007 | Krivoruhko |
| 2007/0276462 A1 | 11/2007 | Iancea et al. |
| 2007/0288089 A1 | 12/2007 | Gurskis |
| 2008/0004398 A1 | 1/2008 | Durrieu et al. |
| 2008/0004696 A1 | 1/2008 | Vesely |
| 2008/0009746 A1 | 1/2008 | Forster |
| 2008/0015687 A1 | 1/2008 | Lashinski et al. |
| 2008/0027483 A1 | 1/2008 | Cartledge et al. |
| 2008/0065011 A1 | 3/2008 | Marchand et al. |
| 2008/0208213 A1 | 8/2008 | Benjamin et al. |
| 2008/0249534 A1 | 10/2008 | Gruber et al. |
| 2008/0255652 A1 | 10/2008 | Thomas |
| 2008/0306586 A1 | 12/2008 | Cartledge et al. |
| 2009/0005760 A1 | 1/2009 | Cartledge et al. |
| 2009/0030501 A1 | 1/2009 | Morris |
| 2009/0099638 A1 | 4/2009 | Grewe |
| 2009/0099649 A1 | 4/2009 | Chobotov et al. |
| 2009/0125098 A1 | 5/2009 | Chuter |
| 2009/0132035 A1 | 5/2009 | Roth et al. |
| 2009/0216314 A1 | 8/2009 | Quadri |
| 2009/0228093 A1 | 9/2009 | Taylor et al. |
| 2009/0234443 A1 | 9/2009 | Ottma et al. |
| 2009/0254165 A1 | 10/2009 | Tabor et al. |
| 2009/0299462 A1 | 12/2009 | Fawzi et al. |
| 2009/0306768 A1 | 12/2009 | Quadri |
| 2010/0030255 A1 | 2/2010 | Berra et al. |
| 2010/0049313 A1 | 2/2010 | Alon et al. |
| 2010/0280495 A1 | 11/2010 | Paul et al. |
| 2010/0331972 A1 | 12/2010 | Pintor et al. |
| 2011/0054519 A1 | 3/2011 | Neuss |
| 2011/0093060 A1 | 4/2011 | Cartledge et al. |
| 2011/0098802 A1 | 4/2011 | Braido et al. |
| 2011/0218619 A1 | 9/2011 | Benichou et al. |
| 2011/0219603 A1 | 9/2011 | White |
| 2011/0224781 A1 | 9/2011 | White |
| 2011/0230956 A1 | 9/2011 | White |
| 2011/0245918 A1 | 10/2011 | White |
| 2011/0251670 A1 | 10/2011 | Kheradvar et al. |
| 2011/0251674 A1 | 10/2011 | Schmid |
| 2011/0288622 A1 | 11/2011 | Chan et al. |
| 2011/0288629 A1 | 11/2011 | White |
| 2012/0035710 A1 | 2/2012 | Hartley |
| 2012/0065723 A1 | 3/2012 | Drasler et al. |
| 2012/0089217 A1 | 4/2012 | Mews et al. |
| 2012/0323316 A1 | 12/2012 | Chau |
| 2013/0046373 A1 | 2/2013 | Cartledge |
| 2013/0158656 A1 | 6/2013 | Sutton |
| 2013/0166017 A1 | 6/2013 | Cartledge |
| 2013/0310923 A1 | 11/2013 | Kheradvar |
| 2014/0018911 A1 | 1/2014 | Zhou |

FOREIGN PATENT DOCUMENTS

| | | |
|---|---|---|
| EP | 836451 A1 | 4/1998 |
| EP | 855883 A1 | 8/1998 |
| EP | 0937439 A3 | 10/1999 |
| EP | 1095634 A2 | 5/2001 |
| EP | 1283027 A2 | 2/2003 |
| EP | 1556116 A2 | 7/2005 |
| EP | 2537487 A1 | 12/2012 |
| JP | 2001129001 A | 5/2001 |
| WO | 9308767 A1 | 5/1993 |
| WO | 9406372 A1 | 3/1994 |
| WO | 9505131 A1 | 2/1995 |
| WO | 9505132 A1 | 2/1995 |
| WO | 9633066 A1 | 10/1996 |
| WO | 9603999 A1 | 12/1996 |
| WO | 9712562 A1 | 4/1997 |
| WO | 9717899 A1 | 5/1997 |
| WO | 9721403 A1 | 6/1997 |
| WO | 97/26829 A1 | 7/1997 |
| WO | 9725000 A1 | 7/1997 |
| WO | 9733532 A2 | 9/1997 |
| WO | 9841167 A1 | 9/1998 |
| WO | 98/49974 A1 | 11/1998 |
| WO | 9915108 A2 | 4/1999 |
| WO | 9943379 A1 | 9/1999 |
| WO | 9947071 A1 | 9/1999 |
| WO | 0033770 A2 | 6/2000 |
| WO | 0071057 A1 | 11/2000 |
| WO | 0074598 A1 | 12/2000 |
| WO | 2001001886 A1 | 1/2001 |
| WO | 0106953 A1 | 2/2001 |
| WO | 0115633 A1 | 3/2001 |
| WO | 0126582 A1 | 4/2001 |
| WO | 0137892 A1 | 5/2001 |
| WO | 0138373 A1 | 5/2001 |
| WO | 0152771 A1 | 7/2001 |
| WO | 02/41789 A2 | 5/2002 |
| WO | 02039925 A2 | 5/2002 |
| WO | 02078569 A2 | 10/2002 |
| WO | 02102234 A2 | 10/2002 |
| WO | 03003945 A2 | 1/2003 |
| WO | 03/018100 A1 | 3/2003 |
| WO | 03/028558 A2 | 4/2003 |
| WO | 03043539 A1 | 5/2003 |
| WO | 03047460 A2 | 6/2003 |
| WO | 03053283 A1 | 7/2003 |
| WO | 03075798 A1 | 9/2003 |
| WO | 03082153 A2 | 10/2003 |
| WO | 03084440 A1 | 10/2003 |
| WO | 2004016193 A2 | 2/2004 |
| WO | 2004016201 A2 | 2/2004 |
| WO | 2004058047 A2 | 7/2004 |
| WO | 2004093746 A1 | 11/2004 |

(56) References Cited

FOREIGN PATENT DOCUMENTS

| | | | |
|---|---|---|---|
| WO | 2004103219 | A2 | 12/2004 |
| WO | 2004105636 | A2 | 12/2004 |
| WO | 2005039445 | A2 | 5/2005 |
| WO | 2005086942 | A2 | 9/2005 |
| WO | 2005115118 | A2 | 12/2005 |
| WO | 2006076325 | A1 | 7/2006 |
| WO | 2006076326 | A2 | 7/2006 |
| WO | 2006076328 | A1 | 7/2006 |
| WO | 2006104859 | A1 | 10/2006 |
| WO | 2006107562 | A2 | 10/2006 |
| WO | 2006128017 | A2 | 11/2006 |
| WO | 2007088549 | A2 | 8/2007 |
| WO | 2007133809 | A2 | 11/2007 |
| WO | 2008016578 | A2 | 2/2008 |
| WO | 2008042266 | A2 | 4/2008 |
| WO | 2008016578 | A3 | 7/2008 |
| WO | 2008/140796 | A1 | 11/2008 |
| WO | 2009046372 | A2 | 4/2009 |
| WO | 2009046372 | A3 | 4/2009 |
| WO | 2009073767 | A1 | 6/2009 |
| WO | 2010/011699 | A3 | 1/2010 |

OTHER PUBLICATIONS

European Search Report of European Patent App. No. 12 84 1445 dated Mar. 11, 2015.
Office action of China Patent App. No. 201180068672.0 dated Jan. 23, 2015.
International Search Report and Written Opinion of the International Searching Authority for International Application PCT/US2014/038305 dated Oct. 10, 2014.
International Search Report and Written Opinion of the International Searching Authority for International Application No. PCT/US2012/061292 dated Jan. 7, 2013.
Extended European Search Report & Search Opinion (PCT/US2007/017061) of the European Patent Office dated Apr. 3, 2013.
International Search Report of PCT/US2011/067695 dated Apr. 25, 2012.
International Search Report of PCT/US2013/027072 dated Apr. 29, 2013.
International Search Report and Written Opinion of the International Searching Authority for International App. No. PCT/US2007/017061 dated Aug. 6, 2008.
Office Action of the Australian Patent office for Application No. 2013260693 dated Dec. 1, 2014.

* cited by examiner

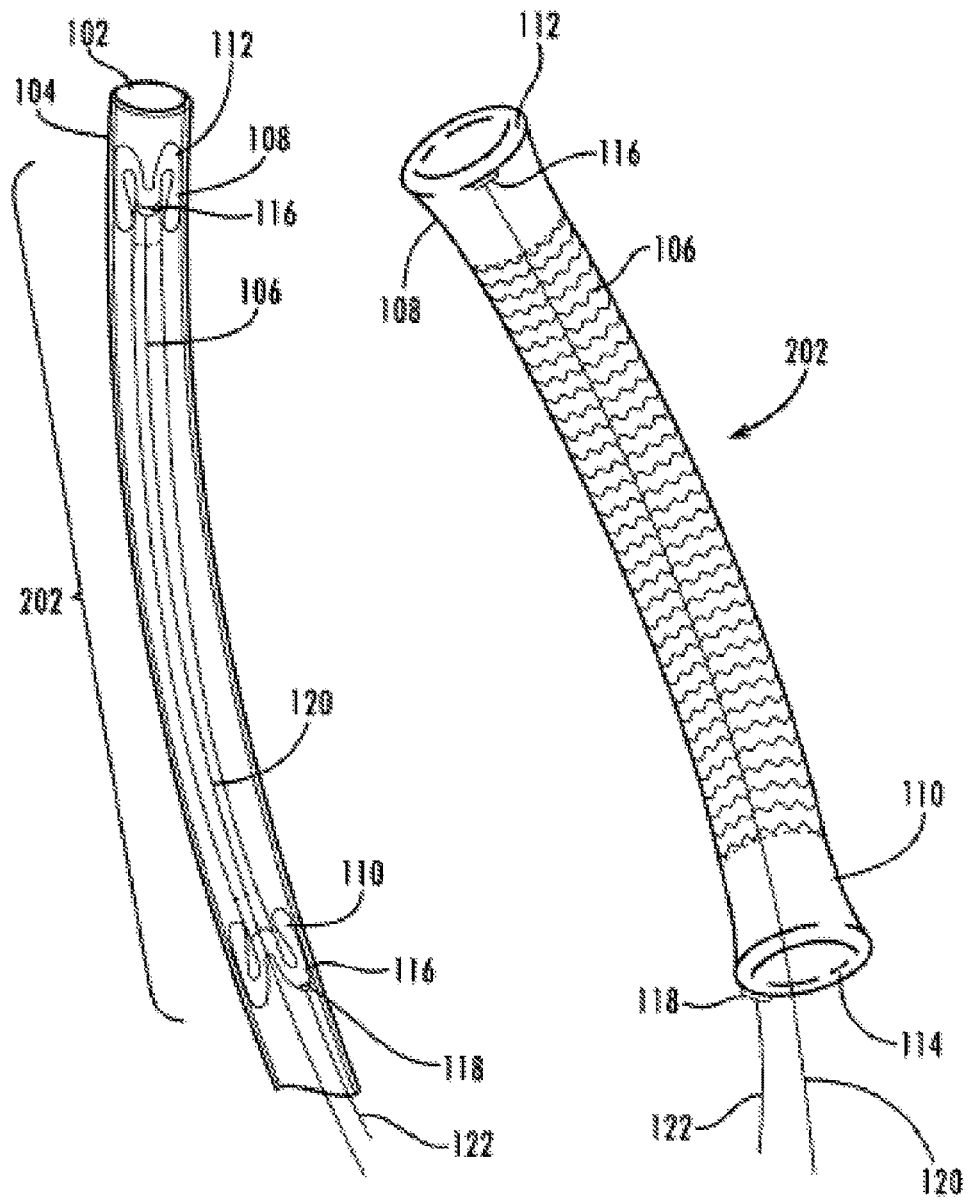

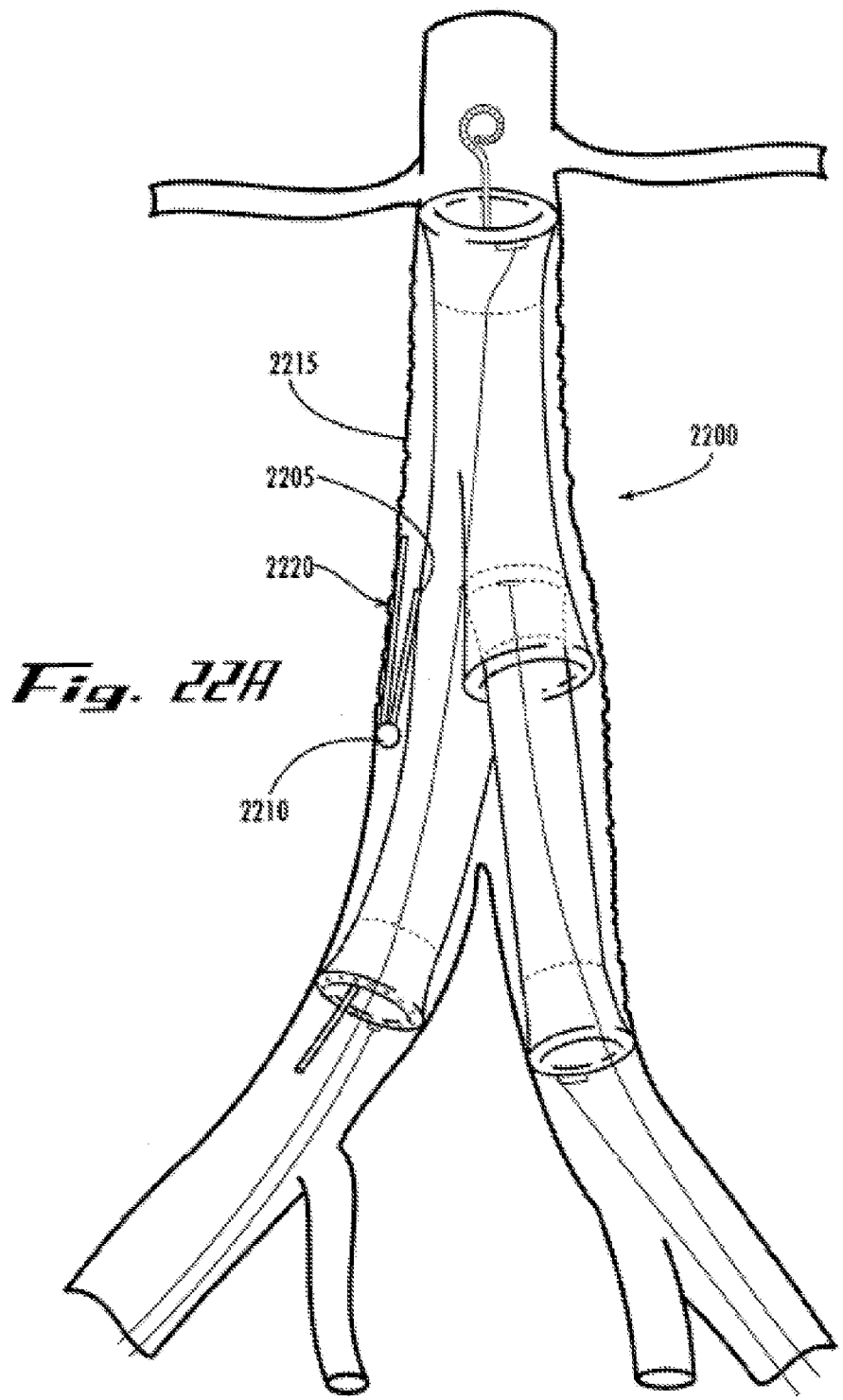

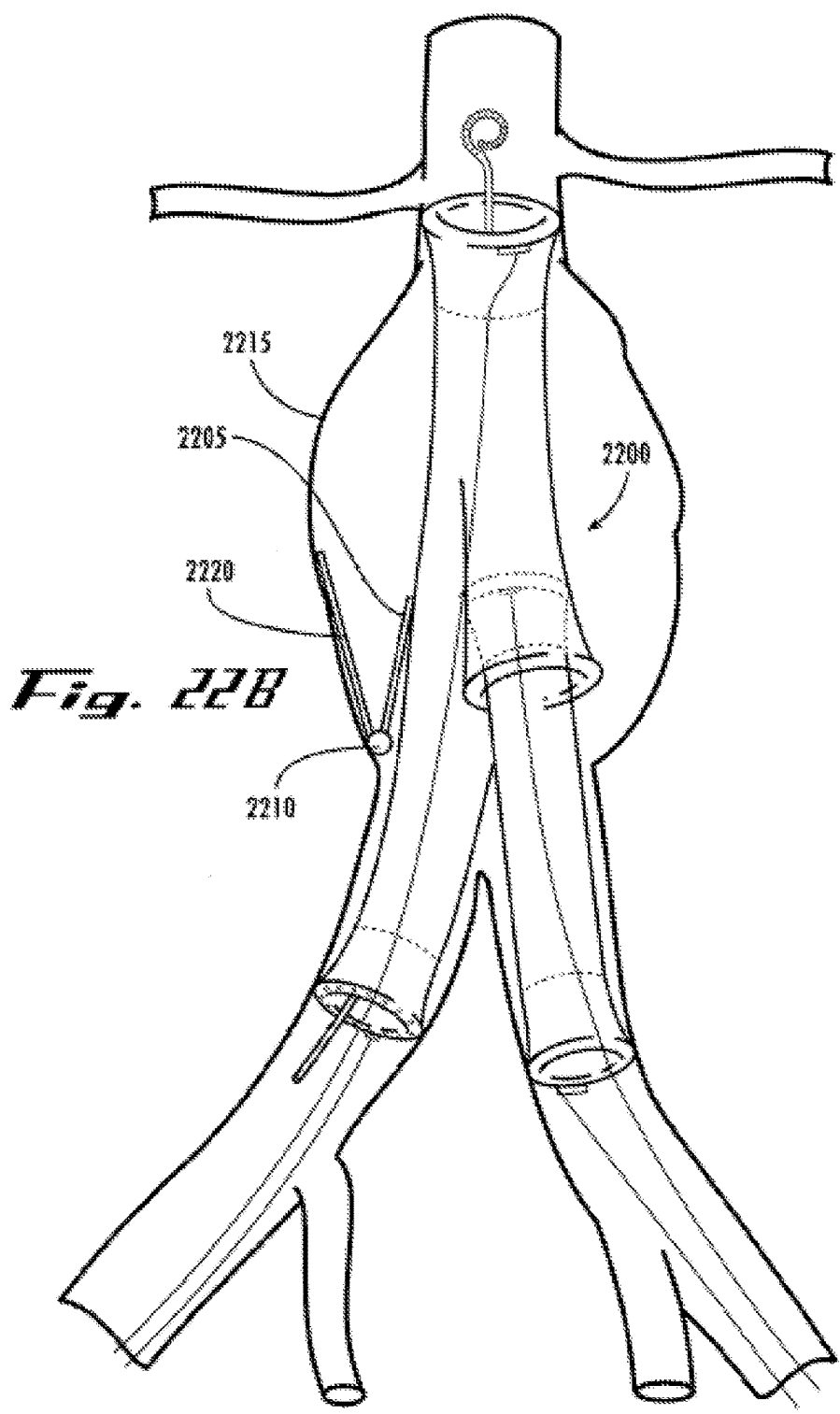

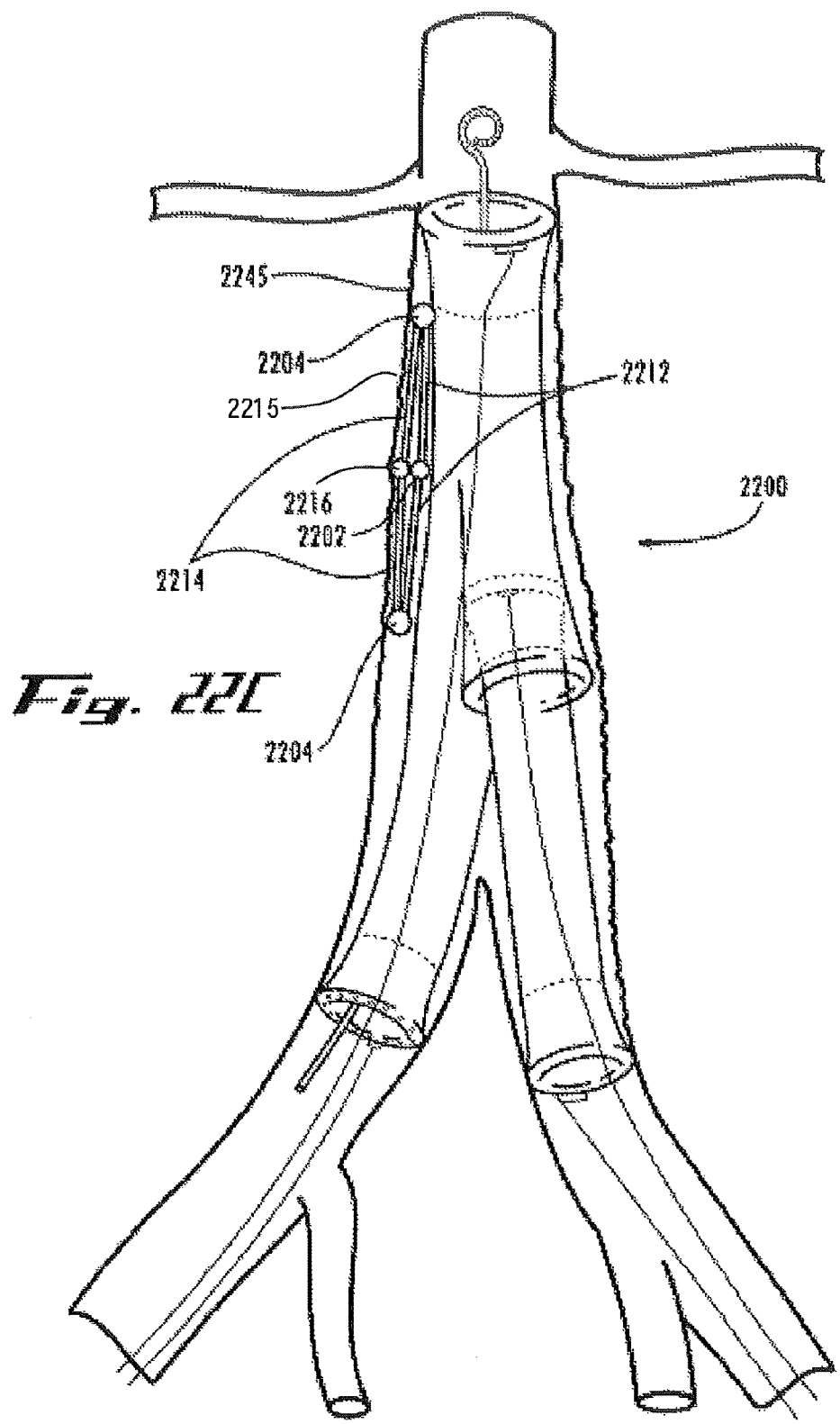

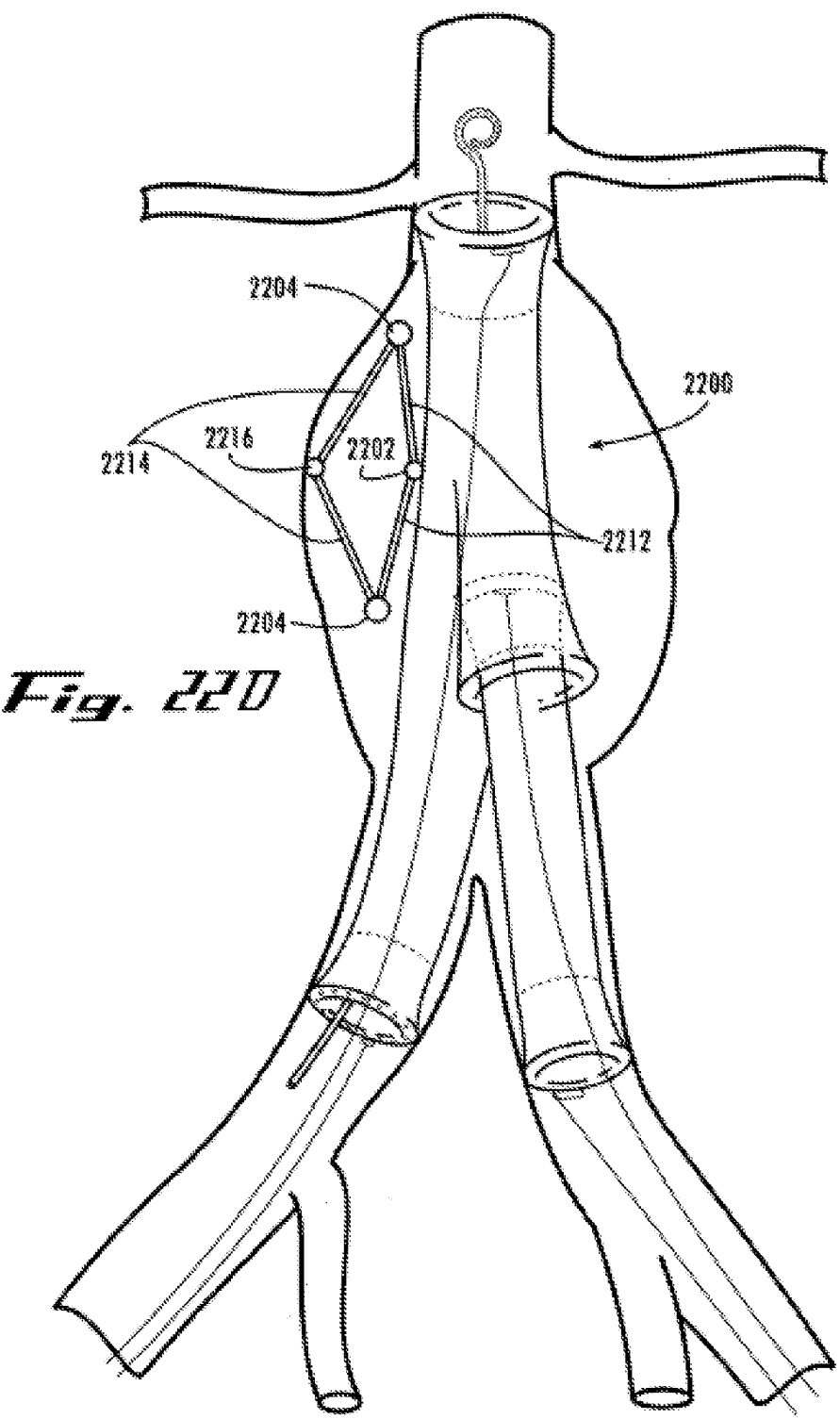

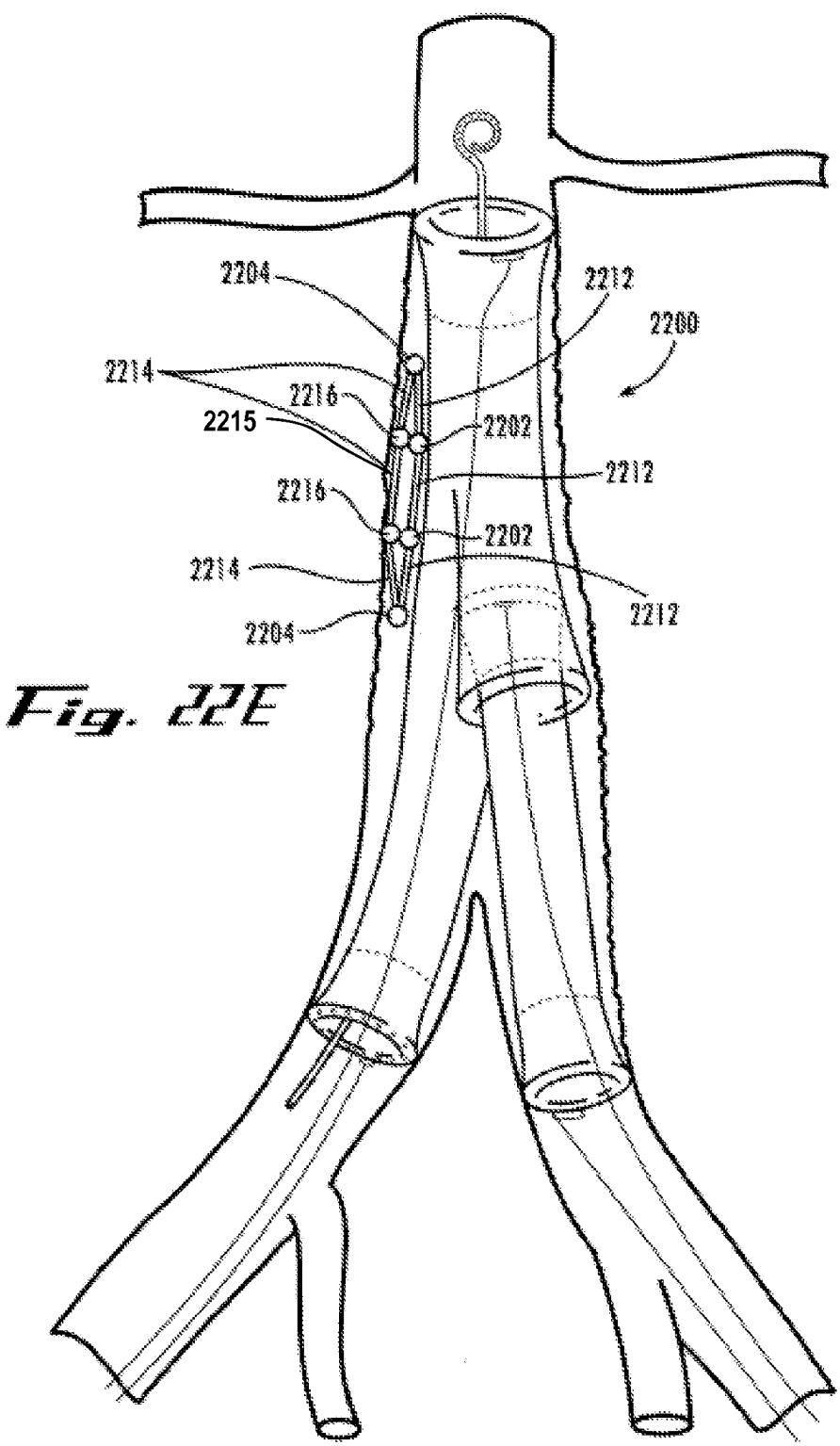

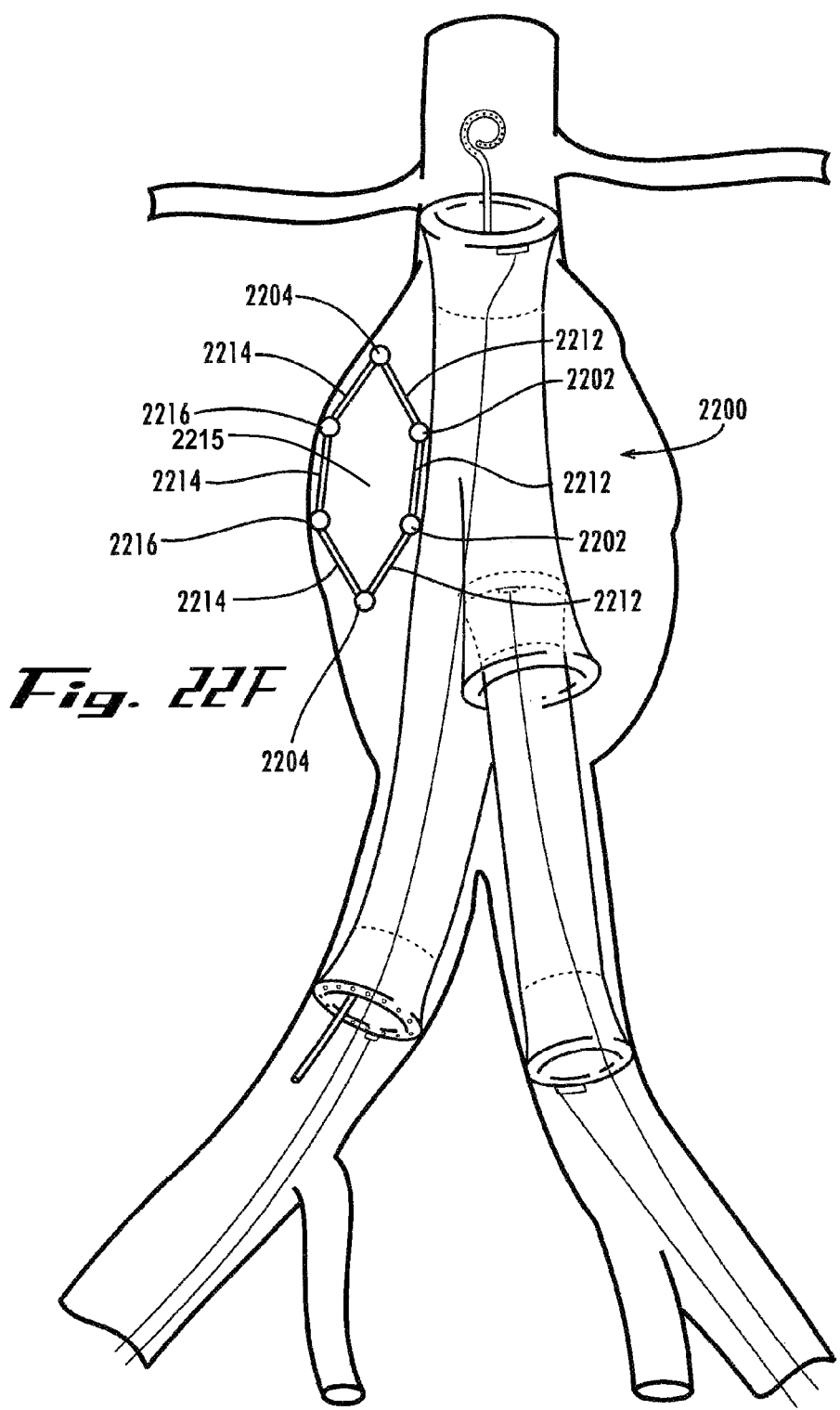

SEALABLE ENDOVASCULAR IMPLANTS AND METHODS FOR THEIR USE

CROSS REFERENCE TO RELATED APPLICATIONS

The present application is:
a divisional application of U.S. patent application Ser. No. 13/544,379, filed Jul. 9, 2012; (now U.S. Pat. No. 9,138,335) and
a divisional application of U.S. patent application Ser. No. 11/888,009, filed Jul. 31, 2007 (now U.S. Pat. No. 8,252,036; which application claims priority of U.S. Provisional Patent Application Ser. No. 60/834,401, filed Jul. 31, 2006, and U.S. Provisional Patent Application Ser. No. 60/834,627, filed Aug. 1, 2006),
the entire disclosures of which are hereby incorporated herein by reference in their entireties.

FIELD OF THE INVENTION

The present invention relates to the field of vascular surgery and the treatment of aneurysms or other luminal vascular defects. Specifically, the present invention relates to a novel design for sealable endovascular implants and to methods of use for such implants in endovascular procedures for aneurysms of the thoracic or abdominal aorta or other vascular structural defects.

BACKGROUND OF THE INVENTION

Aneurysms of the thoracic and abdominal aorta represent a degenerative process of the aorta that is often attributed to atherosclerosis. Aneurysms are defined as a focal dilatation with at least a 50% increase over normal arterial diameter, usually associated with a degradation of the aortic media, or other structural defect in the aortic wall.

Medical research has suggested that these lesions are prone to occur in areas subjected to significant redirection of blood flow during diastole; however, the exact cause of such aneurysms is not known. A familial tendency to symptomatic aneurysms has been suggested. Degenerative aneurysms account for more than 90% of all infrarenal aneurysms of the abdominal aorta. Other potential causes include infection, cystic medial necrosis, arteritis, trauma, collagen vascular disorders, and anastomotic disruption.

Abdominal aortic aneurysms most commonly begin in the infrarenal aorta, and extend down to the iliac bifurcation. Aneurysms of the thoracic aorta are most commonly located in the descending thoracic aorta, beginning just distal to the origin of the left subclavian artery.

Aortic aneurysms generally affect elderly Caucasian men. Aortic aneurysms are less commonly reported among persona of African American, Asian, and Hispanic heritage. Abdominal aortic aneurysms are five times more common in men than in women. In men, the aneurysm process appears to begin at approximately age fifty years and reaches peak incidence at approximately age eighty years. Women appear to have a more delayed onset in which the aneurysm process appears to begin at approximately age 60 years. Smoking has been associated as a potential risk factor for the development of aortic aneurysms. Other risk factors include previous aneurysm repair or peripheral aneurysm (such as femoral or popliteal), coronary artery disease, and hypertension.

Although the reported findings from autopsy series vary widely, the incidence of aortic aneurysms probably exceeds 3-4% in individuals older than 65 years. Death from aneurysmal rupture remains one of the 15 leading causes of death in the United States. In addition, the overall prevalence of aortic aneurysms has increased significantly in the last 30 years. This is partly due to an increase in diagnosis based on the widespread use of imaging techniques. However, the prevalence of fatal and nonfatal rupture has also increased, suggesting a true increase in incidence. An aging population probably plays a significant role.

The surgical management of aortic aneurysms dates back to the early twentieth century, and has involved a variety of methods, including ligation, intraluminal wiring, cellophane wrapping, homografts, and grafts using nylon and polytetrafluoroethylene [PTFE] fabrics.

Prior to the development of endoaneurysmorrhaphy in 1962, postoperative surgical mortality rates were high (>25%). Endovascular repair techniques have reduced the operative mortality to 1.8-5%.

Existing techniques for endovascular treatment of aneurysms involve placement of a tubular graft with seals to normal aortic walls above and below the aneurysm to create a tubular bridge to carry flow across the aneurysm without allowing flow to fill the aneurismal sac. Using these techniques, grafts may be placed using percutaneous access to the femoral arteries, and delivery/implantation using vascular catheters and fluoroscopic visualization. The deficiencies associated with existing endograft technology relate to leakage at the graft/aortic interface and/or post-implantation migration of the endograft. Small post-implantation leaks may be repaired with the placement of one or more extension cuffs above the endograft proximally, or below the implant distally to attempt to obtain a better seal with the vessel. The required use of such cuffs may add significantly to the overall cost and morbidity of the procedure. Major failures with endograft repair generally require emergent open surgery to avert catastrophic rupture of the aneurysm. Also, current endovascular systems require accurate size matching of endograft implants, leaving a very small margin for error.

In order for a patient to be a candidate for existing endograft methods and technologies, a proximal neck of at least 15 mm. of normal aorta must exist between the origin of the most inferior renal artery and the origin of the aneurysm in the case of abdominal aneurysms or the left subclavian artery for thoracic aortic aneurysms in order to permit an adequate seal. Similarly, at least 15 mm. of normal vessel must exist distal to the distal extent of the aneurysm for an adequate seal to be achieved.

Migration of existing endografts has also been a significant clinical problem, potentially causing leakage and re-vascularization of aneurysms and/or compromising necessary vascular supplies to arteries such as the carotid, subclavian, renal, or internal iliac vessels. This problem has been partially addressed by some existing endograft designs, in which barbs or hooks have been incorporated to help retain the endograft at its intended site. However, these existing endograft designs are not removable and repositionable once they are deployed. Thus, once such an endograft has been placed, open surgery is necessary if there is failure due to leakage or undesired occlusion of other vascular structures.

Because of the limitations imposed by existing vascular endograft devices and endovascular techniques, approximately eighty percent of abdominal and thoracic aneurysms repaired in the U.S. are still managed though open vascular surgery, instead of the lower morbidity of the endovascular approach.

SUMMARY OF THE INVENTION

The present invention is directed towards a novel design for endovascular implant grafts, and methods for their use for the treatment of aortic aneurysms and other structural vascular defects. A sealable, repositionable endograft system for placement in a blood vessel is disclosed, in which an endograft implant comprises a non-elastic tubular implant body with an elastic proximal end(s) and an elastic distal end(s). Both the elastic proximal and distal ends in an implant according to the present invention further comprise one or more circumferential sealable collars and one or more variable sealing device, capable of controllably varying the expanded diameter of said collar upon deployment to achieve the desired seal between the collar and the vessel's inner wall. An endovascular implant according to the present invention further comprises a central lumen and one or more control leads extending distally from releasable connections with each variable sealing device. Embodiments of endovascular implants according to the present invention may further be provided with retractable retention tines or other retention devices allowing an implant to be repositioned before final deployment. An endograft system according to the present invention further comprises a delivery catheter with an operable tubular sheath, capable of housing a folded or compressed endograft implant prior to deployment and capable of retracting or otherwise opening in at least its proximal end to allow implant deployment, said sheath sized and configured to allow its placement via a peripheral arteriotomy site, and of appropriate length to allow its advancement into the thoracic or abdominal aorta, as required for a specific application.

In use of an embodiment according to the present invention, an operator prepares an arteriotomy site in a patient in a suitable peripheral location, such as the femoral arteries. Upon incision into the artery, a guide wire is placed, and extended under radiographic visualization into the aorta. A catheter sheath is inserted, housing a collapsed endovascular graft. An injector cannula is inserted, with its proximal tip extending beyond the catheter sheath. Under radiographic visualization, radio-opaque or other contrast dye is injected into the injector cannula, and the contrast dye-enhanced view is used to position the proximal edge of the cannula above the beginning of the aneurysm sac. The catheter sheath is then partially retracted to expose the proximal portion of the endovascular implant. Through action initiated by the operator on the control leads, the variable sealing device for the proximal seal is activated, expanding the elastic circumferential sealable collar until firm contact is made with the vessel wall. At this point, additional radio-opaque or other contrast dye is injected, and the seal is assessed. If there are leaks, the variable sealing device is again activated to expand the diameter of the circumferential sealable collar for a firmer contact. The seal is reassessed and adjusted until there no contrast dye leaks are seen. If the radio-opaque or other contrast dye indicates that the device is placed too proximally and threatens or covers the renal or subclavian junctions, then it is loosened and moved distally.

Once the proximal circumferential sealable collar has been suitably sealed, the catheter sheath is then retracted beyond the distal extent of the aneurysm exposing the remainder of the graft. The variable sealing device for the distal seal is similarly activated, expanding the elastic circumferential sealable collar until firm contact is made with the vessel wall. At this point, additional radio-opaque or other contrast dye is injected, and the distal seal is assessed. If there are leaks, the distal variable sealing device is again activated to expand the diameter of the distal circumferential sealable collar for a firmer contact. The seal is reassessed and adjusted until no contrast dye leaks are seen.

For an implant for an abdominal aortic aneurysm according to the present invention, an endograft implant comprises a non-elastic tubular body with an elastic proximal and distal ends and a non-elastic contralateral cuff. An operator deploys and seals the proximal and distal ends of the implant as described above, with the distal end deployed and sealed in the iliac artery on the side of the initial arteriotomy. Then, a second arteriotomy is made on the opposite side. Radio-opaque or other contrast dye injection is again used to allow visualization of the non-elastic contralateral cuff, and a second guide wire is placed from the second arteriotomy site through the non-elastic contralateral cuff. A contralateral delivery catheter is then introduced over the second guide wire. The contralateral delivery catheter comprises a slidable or removable sheath housing a folded or compressed endograft segmental implant which further comprises a non-elastic tubular body with an elastic proximal and distal ends. Both the elastic proximal and distal ends in an endograft segmental implant according to the present invention further comprise one or more circumferential sealable collars and one or more variable sealing device, capable of controllable varying the expanded diameter of said collar upon deployment to achieve the desired seal between the collar and the non elastic contralateral cuff proximally and between the collar and the vessel's inner wall distally. An endograft segmental implant according to the present invention further comprises a central lumen and one or more control leads extending distally from releasable connections with each variable sealing device.

Again, under radiographic control, radio-opaque or other contrast dye is injected into the injector cannula, and the contrast dye-enhanced view is used to position the proximal edge of the contralateral delivery catheter within the lumen of the non-elastic contralateral cuff. The contralateral delivery catheter sheath is then partially retracted to expose the proximal portion of the endograft segmental implant. Through action initiated by the operator on the control leads, the variable sealing device for the proximal seal is activated, expanding the elastic circumferential sealable collar until firm contact is made between the sealable collar and the non-elastic cuff. At this point, additional radio-opaque or other contrast dye is injected, and the seal is assessed. If there are leaks, the variable sealing device is again activated to expand the diameter of the circumferential sealable collar for a firmer contact. The seal is reassessed and adjusted until no contrast dye leaks are seen.

Finally, once the proximal circumferential sealable collar of the endograft segmental implant has been suitably sealed, the catheter sheath is then retracted beyond the distal extent of the aneurysm, exposing the remainder of the graft. The variable sealing device for the distal seal is similarly activated, expanding the elastic circumferential sealable collar until firm contact is made with the vessel wall. At this point, additional radio-opaque or other contrast dye is injected, and the distal seal is assessed. If there are leaks, the distal variable sealing device is again activated to expand the diameter of the distal circumferential sealable collar for a firmer contact. The seal is reassessed and adjusted until no contrast dye leaks are seen. At this point, the operator may remove the injector cannula and detach the control leads from the variable sealing devices, and remove the control leads and guide wires from their arteriotomy sites and close the wounds.

With the foregoing and other objects in view, there is provided, a sealable vascular endograft system for placement in a vascular defect including an elongated implant delivery catheter having a catheter proximal end and a catheter distal end and shaped to be disposed within a blood vessel having internal walls. The implant delivery catheter includes an implant delivery catheter sheath defining an implant delivery catheter lumen and an endovascular implant removably disposed within the implant delivery catheter lumen in a compressed or folded state for delivery thereof to the vascular defect. The endovascular implant includes a tubular implant body and a sealable circumferential collar at the tubular implant body and including a variable sealing device and a control lead traversing from the variable sealing device to a user and controlling variability of the variable sealing device by the user. The variable sealing device and the control lead cooperate to reversibly expand and contract the sealable circumferential collar such that the sealable circumferential collar circumferentially adjusts during deployment thereof to achieve a repositionable fluid-tight seal between the sealable circumferential collar and the internal walls of the blood vessel.

In accordance with another feature, the tubular implant body is non-elastic and the sealable circumferential collar is elastic.

In accordance with a further feature, the sealable circumferential collar is a proximal sealable circumferential collar to be deployed proximal to the vascular defect and the tubular implant body has a distal end, and further comprising a distal sealable circumferential collar at the distal end of the tubular implant body, the distal sealable circumferential collar including a distal variable sealing device reversibly expanding and contracting the distal sealable circumferential collar to circumferentially adjust the distal sealable circumferential collar during deployment thereof to achieve a repositionable fluid-tight seal between the distal sealable circumferential collar and internal walls of the blood vessel distal to the vascular defect.

In accordance with an added feature, the tubular implant body has a distal end, and which further comprises a distal variable sealing device at the distal end of the tubular implant body and a distal control lead connected to the distal variable sealing device, the distal control lead traversing the implant delivery catheter from the distal variable sealing device at least to the catheter proximal end when housed therein for interface by the user.

In accordance with an additional feature, the tubular implant body is straight.

In accordance with yet another feature, the tubular implant body branches into two or more branches.

In accordance with yet a further feature, the tubular implant body is a plurality of tubular implant bodies each operable to be connected to another of the tubular implant bodies in a variably sealable manner by operation of the respective sealable circumferential collar as controlled by the respective variable sealing device to achieve a repositionable fluid-tight seal between a proximal-most one of the sealable circumferential collars and the internal walls of the blood vessel proximal to the vascular defect and a distal-most one of the sealable circumferential collars and the internal walls of the blood vessel distal to the vascular defect.

In accordance with yet an added feature, the tubular implant body is of solid construction and a biocompatible material.

In accordance with yet an additional feature, the tubular implant body is of woven construction and a biocompatible material.

In accordance with again another feature, the endovascular implant is coated with a biocompatible material.

In accordance with again a further feature, the endovascular implant further comprises a retraction device to reposition the endovascular implant during deployment.

In accordance with again an added feature, there is provided a retraction device repositioning the tubular implant body during deployment.

With the objects in view, there is also provided a method of treating a vascular defect in a blood vessel within a patient, the method comprising the steps of providing an endovascular implant with a tubular implant body, a sealable circumferential collar at the tubular implant body and having a variable sealing device to reversibly expand and contract the sealable circumferential collar, and a control lead operatively connected to the variable sealing device to reversibly expand and contract the sealable circumferential collar, the control lead traversing from the variable sealing device to a user for interface by the user when the endovascular implant is at the vascular defect, guiding the endovascular implant in a compressed or folded state to the vascular defect, cooperatively manipulating the control lead and the variable sealing device to circumferentially adjust the sealable circumferential collar to achieve a fluid-tight seal between the sealable circumferential collar and the internal walls of the blood vessel adjacent the vascular defect, the manipulation of the control lead and the variable sealing device reversibly expanding and contracting the sealable circumferential collar during deployment thereof to reposition the fluid-tight seal, and removing the control lead from the patient.

In accordance with again an additional mode, the sealable circumferential collar is a proximal sealable circumferential collar, the tubular implant body has a distal end, and which further comprises the steps of providing a distal sealable circumferential collar at the distal end of the tubular implant body, the distal sealable circumferential collar including a distal variable sealing device operating to reversibly expand and contract the distal sealable circumferential collar when controlled, operatively connecting a distal control lead to the distal variable sealing device to reversibly expand and contract the sealable circumferential collar, the distal control lead traversing from the distal variable sealing device to a user for interface by the user when the endovascular implant is at the vascular defect, and cooperatively manipulating the distal control lead and the distal variable sealing device to circumferentially adjust the distal sealable circumferential collar to achieve a fluid-tight distal seal between the distal sealable circumferential collar and the internal walls of the blood vessel adjacent the vascular defect, the manipulation of the distal control lead and the distal variable sealing device reversibly expanding and contracting the distal sealable circumferential collar during deployment thereof to reposition the fluid-tight distal seal.

In accordance with still another mode, there is provided the step of connecting one or more additional endovascular implants in a variably sealable manner by operation of the sealable circumferential collars as controlled by the respective variable sealing devices and control leads to achieve a repositionable fluid-tight seal between a proximal-most one of the sealable circumferential collars and the internal walls of the blood vessel proximal to the vascular defect and a distal-most one of the sealable circumferential collars and the internal walls of the blood vessel distal to the vascular defect.

In accordance with a concomitant feature, the vascular defect is an aneurysm.

The preceding description is presented only as an exemplary application of the devices and methods according to the present invention.

BRIEF DESCRIPTION OF THE DRAWINGS

FIG. 2A is a side perspective view of the proximal tip of a delivery catheter containing a disclosed embodiment of the present invention of a compressed or folded endograft segmental implant housed within a sheath of the present invention.

FIG. 2B is a side perspective view of the proximal tip of a delivery catheter containing a disclosed embodiment of the present invention of a decompressed or unfolded endograft segmental implant removed from a sheath of the present invention.

FIG. 22A is a longitudinal anatomic view of a disclosed embodiment according to the present invention of an endovascular implant incorporating an endograft monitoring device attached to the aneurysmal sac wall and the outer wall of the endograft in which the endograft has been effectively sealed in position proximally and distally to an aneurysm, thus devascularizing the aneurysmal sac to allow the walls of the aneurysm to collapse against the endograft, and hold the endograft monitoring device in a collapsed position.

FIG. 22B is a longitudinal anatomic view of a disclosed embodiment according to the present invention of an endovascular implant incorporating an endograft monitoring device of FIG. 22A in which the aneurysmal sac has become revascularized, allowing the endograft monitoring device to spring open such that it may be visualized on x-ray or other diagnostic visualization means.

FIG. 22C shows an alternate embodiment of an endovascular implant incorporating an endograft monitoring device according to the present invention, in which said endograft monitoring device comprises more than one spring-like attachment to both the outer wall of the endograft and to the inner wall of the aneurysmal sac, and in which the aneurysmal sac has been sealed and devascularized, allowing the walls of the aneurysm to collapse against the endograft, and hold the endograft monitoring device in a collapsed position.

FIG. 22D shows the alternate embodiment of an endovascular implant incorporating an endograft monitoring device according to the present invention of FIG. 22C, in which said endograft monitoring device comprises more than one spring-like attachment to both the outer wall of the endograft and to the inner wall of the aneurysmal sac, and in which the aneurysmal sac has become revascularized, allowing the endograft monitoring device to spring open such that it may be visualized on x-ray or other diagnostic visualization means.

FIG. 22E shows yet another an alternate embodiment of an endovascular implant incorporating an endograft monitoring device according to the present invention, in which said endograft monitoring device comprises a plurality of spring-like attachment to both the outer wall of the endograft and to the inner wall of the aneurysmal sac, and in which the aneurysmal sac has been sealed and devascularized, allowing the walls of the aneurysm to collapse against the endograft, and hold the endograft monitoring device in a collapsed position.

FIG. 22F shows the embodiment of an endovascular implant incorporating an endograft monitoring device according to the present invention of FIG. 22E, in which said endograft monitoring device comprises more than one spring-like attachment to both the outer wall of the endograft and to the inner wall of the aneurysmal sac, and in which the aneurysmal sac has become revascularized, allowing the endograft monitoring device to spring open such that it may be visualized on x-ray or other diagnostic visualization means.

DETAILED DESCRIPTION OF INVENTION

Figure 1A:
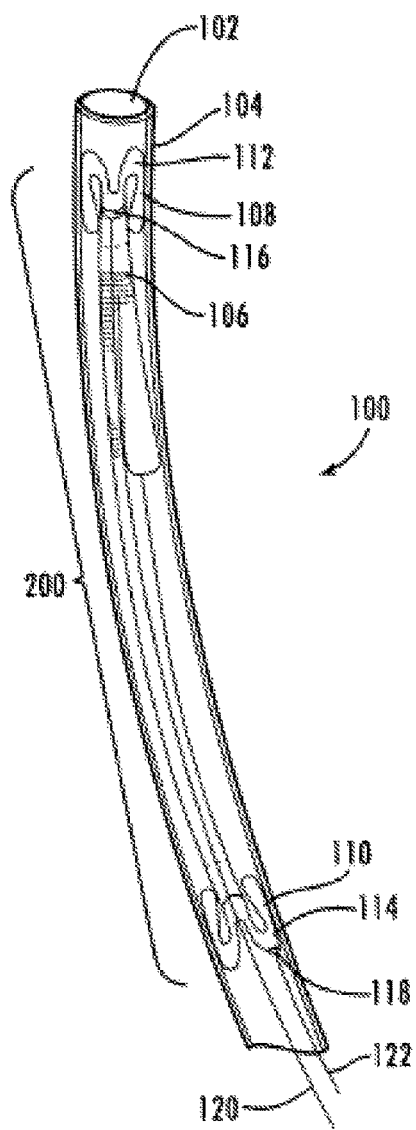
FIG. 1A is a side perspective view of the proximal tip of a delivery catheter containing a disclosed embodiment of the present invention of a compressed or folded bifurcated endovascular implant with a contralateral cuff housed within a sheath.

The present invention may be understood more readily by reference to the following detailed description of the preferred embodiments of the invention and the examples included herein. However, before the preferred embodiments of the devices and methods according to the present invention are disclosed and described, it is to be understood that this invention is not limited to the exemplary embodiments described within this disclosure, and the numerous modifications and variations therein that will be apparent to those skilled in the art remain within the scope of the invention disclosed herein. It is also to be understood that the terminology used herein is for the purpose of describing specific embodiments only and is not intended to be limiting.

Unless otherwise noted, the terms used herein are to be understood according to conventional usage by those of ordinary skill in the relevant art. In addition to the definitions of terms provided below, it is to be understood that as used in the specification and in the claims, "a" or "an" can mean one or more, depending upon the context in which it is used.

The present invention is directed towards novel designs for sealable and repositionable endovascular implant grafts, and methods for their use for the treatment of aortic aneurysms and other structural vascular defects.

In an exemplary embodiment according to the present invention, a sealable vascular endograft system for placement in a vascular defect is provided, comprising an elongated main implant delivery catheter with an external end and an internal end for placement in a blood vessel with internal walls. In such an exemplary embodiment, the main implant delivery catheter further comprises a main implant delivery catheter sheath which may be openable or removable at said internal end and a main implant delivery catheter lumen containing within a compressed or folded endovascular implant. Further, in such an exemplary embodiment, an endovascular implant comprises a non-elastic tubular implant body with an elastic proximal end terminating in a proximal sealable circumferential collar controlled by a proximal variable sealing device which is operated by a proximal control lead that traverses said main implant delivery catheter and exits at said external end for interface by an operator, such that said proximal sealable circumferential collar may be expanded or contracted by said operator to achieve a fluid-tight seal between said proximal sealable circumferential collar and the internal walls of said blood vessel proximal to said vascular defect. Moreover, in such an exemplary embodiment, an endovascular implant further comprises a non-elastic tubular implant body with an elastic distal end terminating in a distal sealable circumferential collar controlled by a distal variable sealing device which is operated by a distal control lead that exits said main implant delivery catheter at said external end for interface by an operator, such that said distal sealable circumferential collar may be expanded or contracted by said operator to achieve a fluid-tight seal between said distal sealable circumferential collar and the internal walls of said blood vessel distal to the vascular defect.

Referring now in more detail to the drawings, in which like numerals indicate like elements throughout the several views, FIG. 1A shows a side perspective view of the proximal tip of a main implant delivery catheter 100 with a main implant delivery catheter lumen 102 containing a disclosed embodiment of compressed or folded endovascular implant 200 housed within a main implant delivery catheter sheath 104. The endovascular implant 200 in the embodiment shown in FIG. 1A includes a non-elastic tubular implant body 106 with an elastic proximal end 108 and an elastic distal end 110. The elastic proximal end 108 terminates in a proximal sealable circumferential collar 112, controlled by a proximal variable sealing device 116 which is operated by a proximal control lead 120 that traverses the main implant delivery catheter 100 and exits distally for interface with an operator (not shown in FIG. 1A). The elastic distal end 110 terminates in a distal sealable circumferential collar 114, controlled by a distal variable sealing device 118 which is operated by a distal control lead 122 that exits the main implant delivery catheter 100 distally for interface with an operator (not shown in FIG. 1A).

Figure 1B:
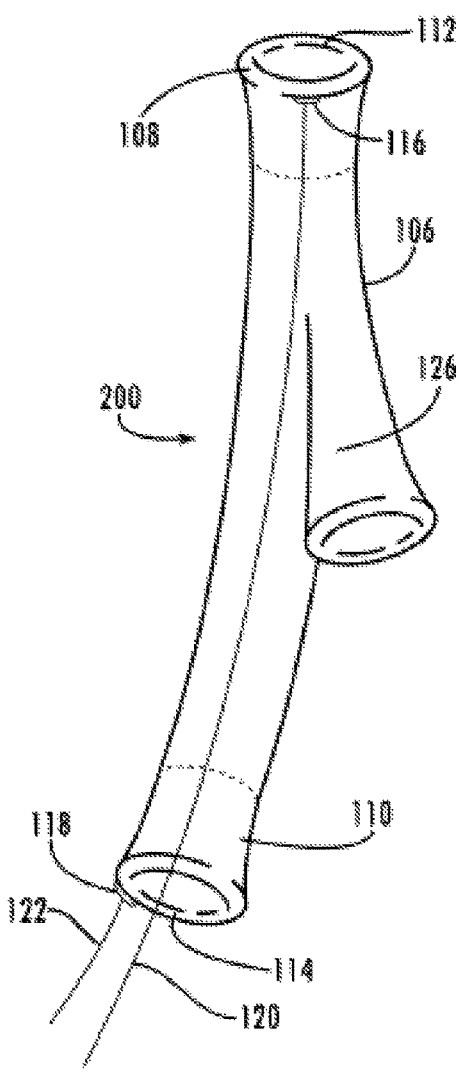
FIG. 1B is a side perspective view of the proximal tip of a delivery catheter containing a disclosed embodiment of the present invention of a decompressed or unfolded endovascular implant removed from a sheath.

The embodiment of an endovascular implant 200 of FIG. 1A is further shown in FIG. 1B removed from the main implant delivery catheter 100 and in a semi- or partially expanded or non-folded state. In addition to the elements described in FIG. 1A, the endovascular implant 200 in the embodiment shown in FIG. 1B may also include a contralateral non-elastic cuff 126.

An alternate embodiment of a sealable endovascular implant according to the present invention is shown in FIG. 2A. The proximal tip of a main implant delivery catheter 100 with a main implant delivery catheter lumen 102 containing a disclosed embodiment of compressed or folded straight endovascular implant 202 housed within a main implant delivery catheter sheath 104. The endovascular implant 202 in the embodiment shown in FIG. 2A includes a non-elastic tubular implant body 106 with an elastic proximal end 108 and an elastic distal end 110. The elastic proximal end 108 terminates in a proximal sealable circumferential collar 112, controlled by a proximal variable sealing device 116 which is operated by a proximal control lead 120 that traverses the main implant delivery catheter 100 and exits distally for interface with an operator (not shown in FIG. 2A). The elastic distal end 110 terminates in a distal sealable circumferential collar 114, controlled by a distal variable sealing device 118 which is operated by a distal control lead 122 that exits the main implant delivery catheter 100 distally for interface with an operator (not shown in FIG. 2A).

The embodiment of an endovascular implant 202 of FIG. 2A is further shown in FIG. 2B removed from the main implant delivery catheter 100 and in a semi- or partially expanded or non-folded state. A straight endovascular implant 202 according to the embodiment shown in FIGS. 2A and 2B provides a non-branching conduit between the proximal sealable circumferential collar 112 and the distal sealable circumferential collar 114.

Figure 3:
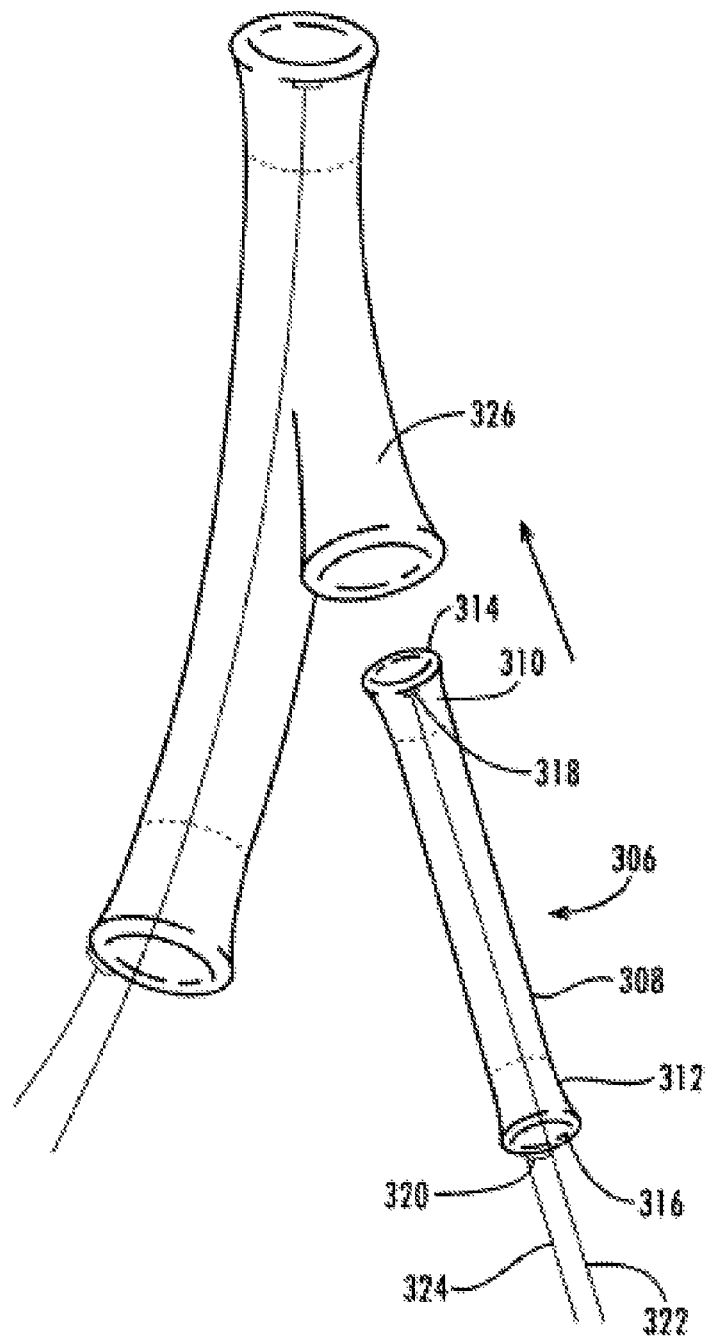
FIG. 3 is a side perspective view of a disclosed embodiment of the present invention of an endograft segmental implant.

An embodiment of an endograft segmental implant according to the present invention is shown in FIG. 3. An endograft segmental implant 306 sealably interfaces to provide a conduit between a non-elastic vascular graft and a distal blood vessel. As shown in FIG. 3, an endograft segmental implant 306 includes a non-elastic tubular segmental implant body 308 with an elastic proximal segmental end 310 and an elastic distal segmental end 312. The elastic proximal segmental end 310 terminates in a proximal segmental sealable circumferential collar 314, controlled by a proximal segmental variable sealing device 318 which is operated by a proximal segmental control lead 322 that traverses a segmental implant delivery catheter (not shown in FIG. 3) and exits distally for interface with an operator (not shown in FIG. 3). The elastic distal segmental end 312 terminates in a distal sealable segmental circumferential collar 316, controlled by a distal segmental variable sealing device 320 which is operated by a distal segmental control lead 324 that exits a segmental implant delivery catheter distally for interface with an operator (not shown in FIG. 3).

In various embodiments according to the present invention, endovascular implants 200 may be constructed of solid, woven, non-woven, or mesh materials such as, but not limited to, natural or synthetic rubbers, nylon, Goretex, elastomers, polyisoprenes, polyphosphazenes, polyurethanes, vinyl plastisols, acrylic polyesters, polyvinylpyrrolidone-polyurethane interpolymers, butadiene rubbers, styrene-butadiene rubbers, rubber lattices, Dacron, PTFE, malleable metals, other biologically compatible materials or a combination of such biologically compatible materials in a molded, woven, or non-woven configuration, coated, non-coated, and other polymers or materials with suitable resilience and pliability qualities. In certain preferred embodiments according to the present invention, it is desirable for the non-elastic tubular implant body 106 and corresponding structures to be pliable to allow for folding or compressibility without allowing elasticity. In certain preferred embodiments according to the present invention, it is desirable for the elastic proximal end 108 and the elastic distal end 110 and corresponding structures to be both elastic and compressible or foldable. In any given preferred embodiment, the non-elastic tubular implant body 106, the elastic proximal end 108, the elastic distal end 110 and corresponding structures may be constructed of the same material of varying elasticity, or these structures may be constructed of different, but compatible materials.

FIGS. 4-9 illustrate an exemplary embodiment of sealable endovascular implants and an illustrative method of their use according to the present invention for the treatment of an infrarenal abdominal aortic aneurysm with vascular access through bilateral femoral arteriotomy sites.

Figure 4:
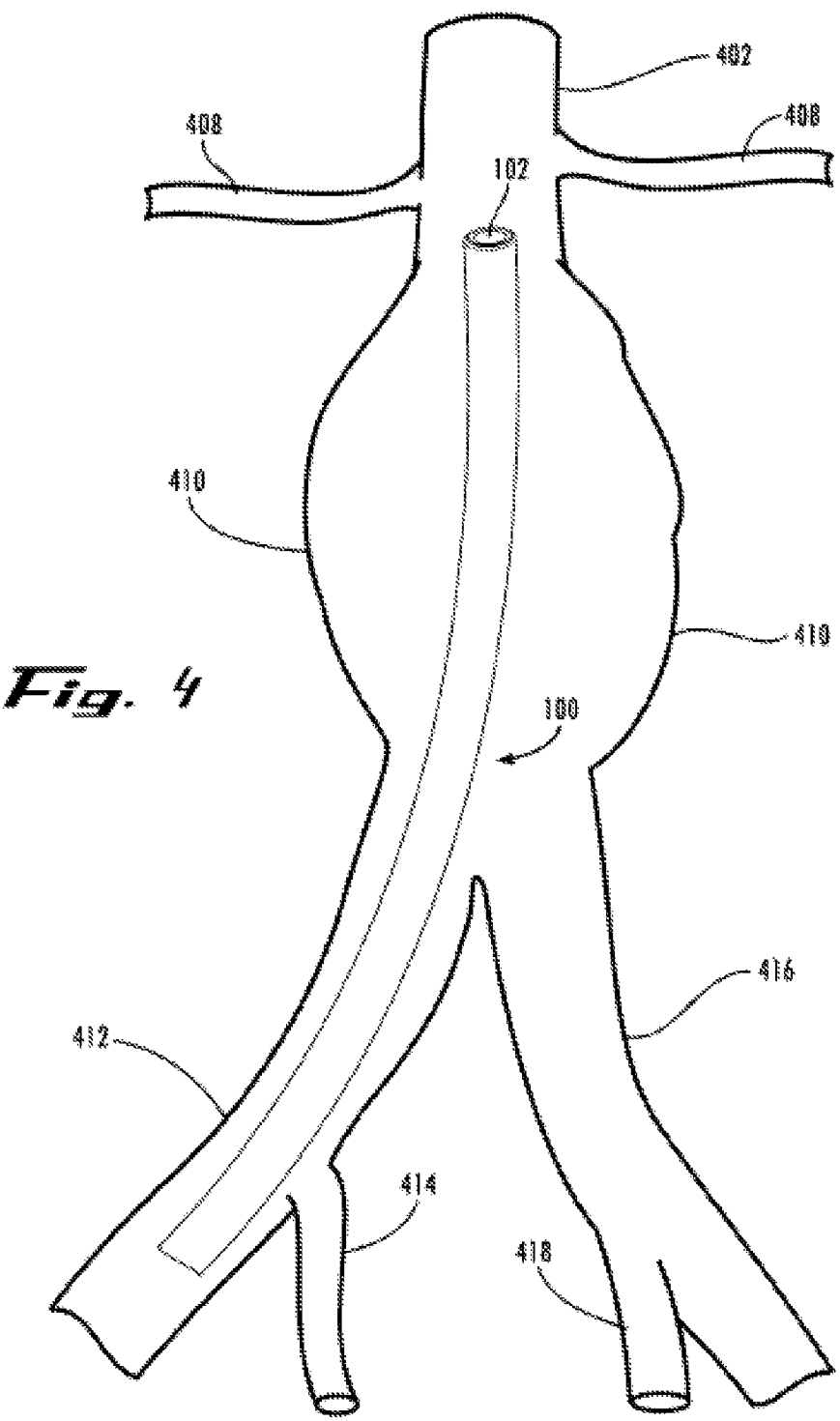
FIG. 4 is a perspective anatomic view of a disclosed embodiment of the present invention in which the proximal tip of an implant delivery catheter placed in a first side through a femoral artery is positioned in an abdominal aorta in an infrarenal location, but above the origin of an abdominal aortic aneurysm.

In FIG. 4, a main implant delivery catheter 100 has been placed in a first side through a femoral artery (not shown in FIG. 4) and positioned in an abdominal aorta 402 in a location distal to the renal arteries 408, but above the origin of an abdominal aortic aneurysm 410.

Figure 5:
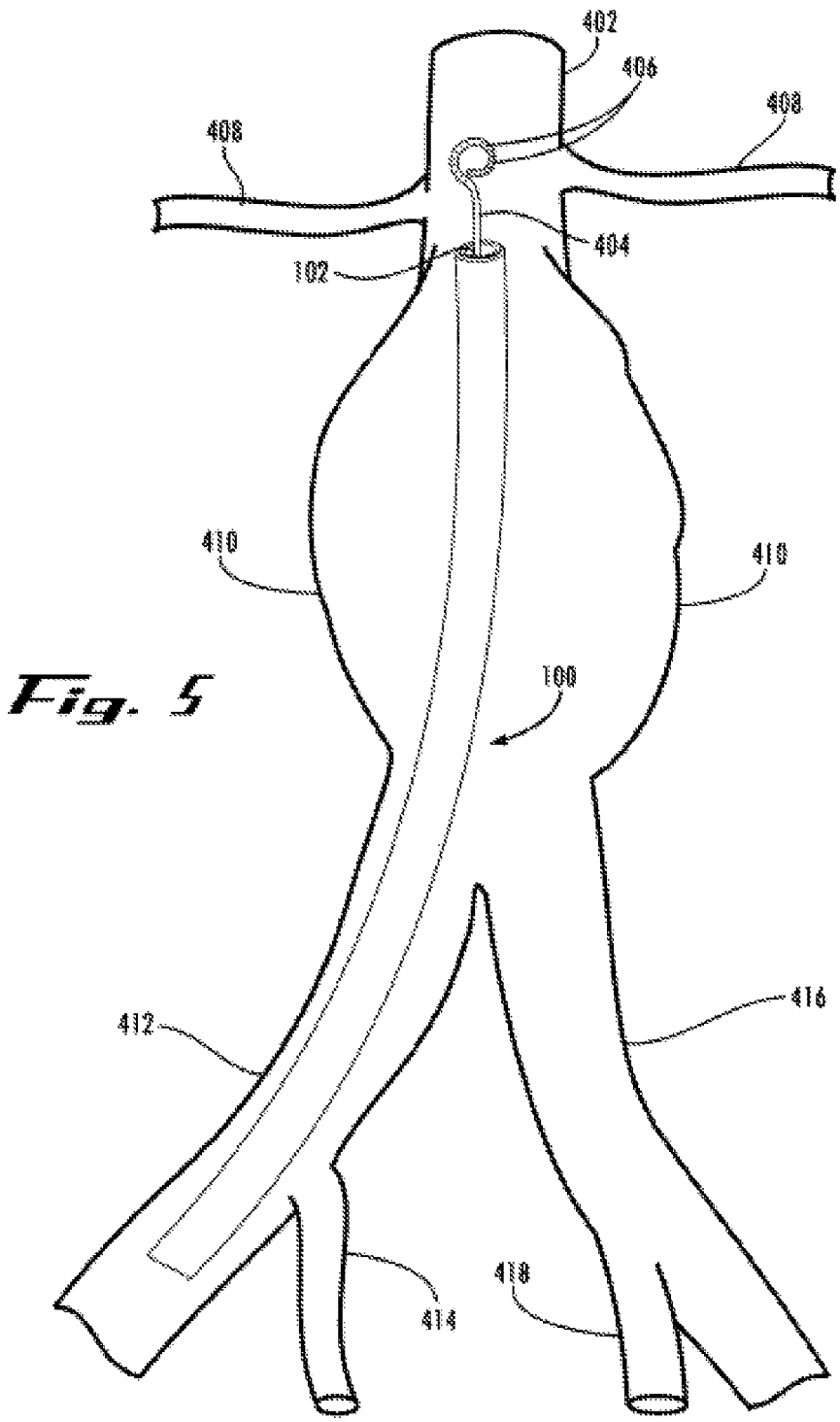
FIG. 5 is a perspective anatomic view of the disclosed embodiment of the present invention of FIG. 4 in which an injector cannula has been introduced through a lumen of the implant delivery catheter, and protrudes proximal to the tip of the implant delivery catheter to fully expose all injector ports for radio-opaque contrast dye injection therethrough.

FIG. 5 is a continuation of the disclosed embodiment of the present invention of FIG. 4 in which an injector cannula 404 with one or more injection ports 406 has been introduced through a main implant delivery lumen 102 of the main implant delivery catheter 100, and protrudes proximal to the tip of the implant delivery catheter 100 to fully expose the injector ports 406 for real-time visualization contrast dye injection therethrough. Such contrast dye injection may be performed using radio-opaque or other contrast dyes for fluoroscopy, computerized tomography, or other radiographic techniques. In alternate embodiments according to the present invention, other real-time visualization techniques may be used, including but not limited to, ultrasound or nuclear magnetic resonance techniques using appropriate contrast dye materials for injection. Such contrast dye injection allows an operator to assess the distance between the origins of the renal arteries 408, and the origin of the aortic aneurysmal sac 410 for proper implant placement.

Figure 6:
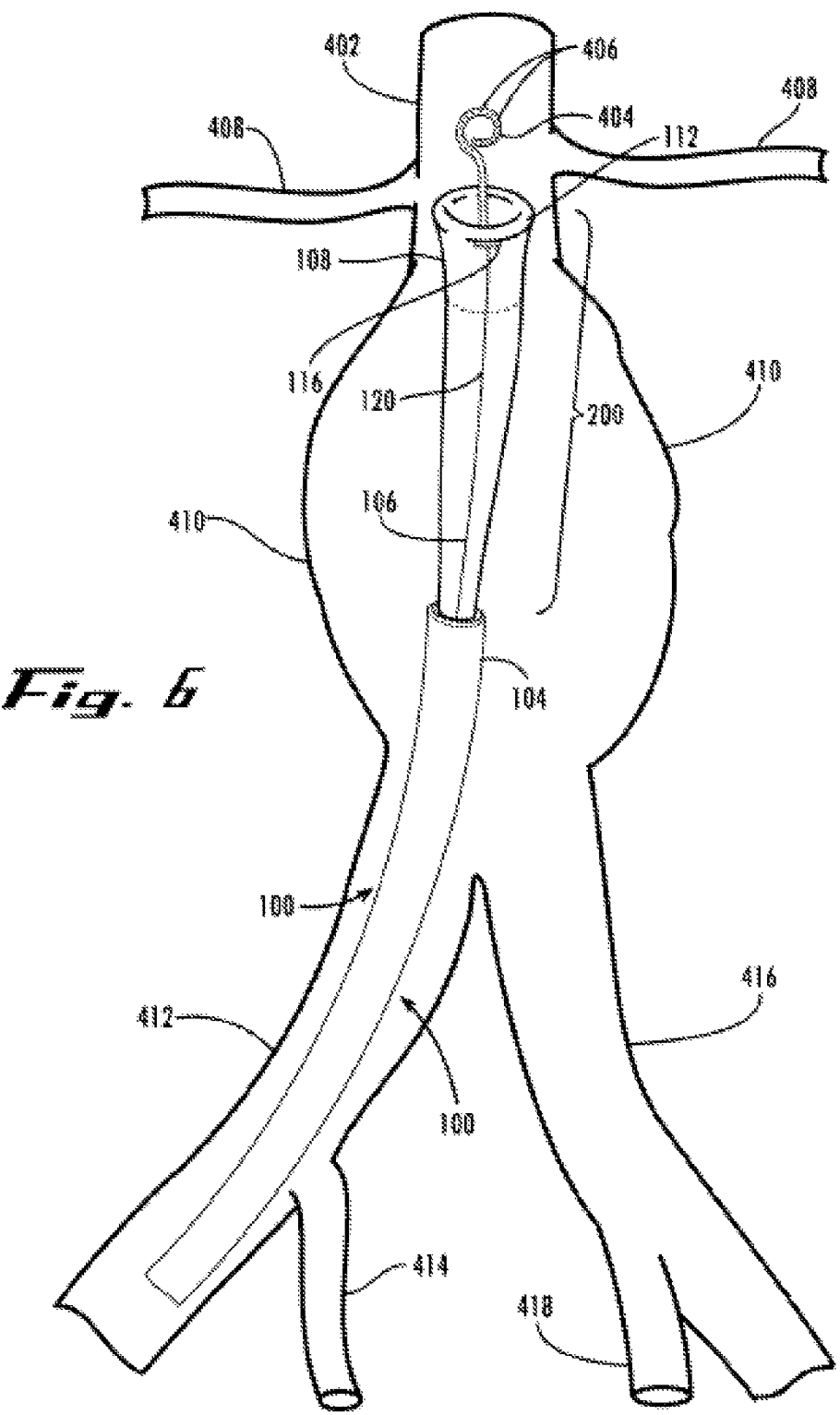
FIG. 6 is a perspective anatomic view of the disclosed embodiment of the present invention of FIG. 5 in which the sheath of the implant delivery catheter has been retracted or partially opened to allow the endograft implant therein to partially decompress or unfold, to expose the proximal elastic implant end and a length of the non-elastic tubular body.

FIG. 6 is a continuation of the disclosed embodiment of the present invention of FIG. 5 in which the main implant delivery catheter sheath 104 of the main implant delivery catheter 100 has been retracted or partially opened to allow the endovascular implant 200 therein to partially open or unfold from its initially compressed or folded position. Additional contrast dye injection through the injector cannula 404 may be performed by the operator at this point to verify the level of the proximal circumferential sealable collar 112 with respect to the level of the renal arteries 408.

Figure 7:
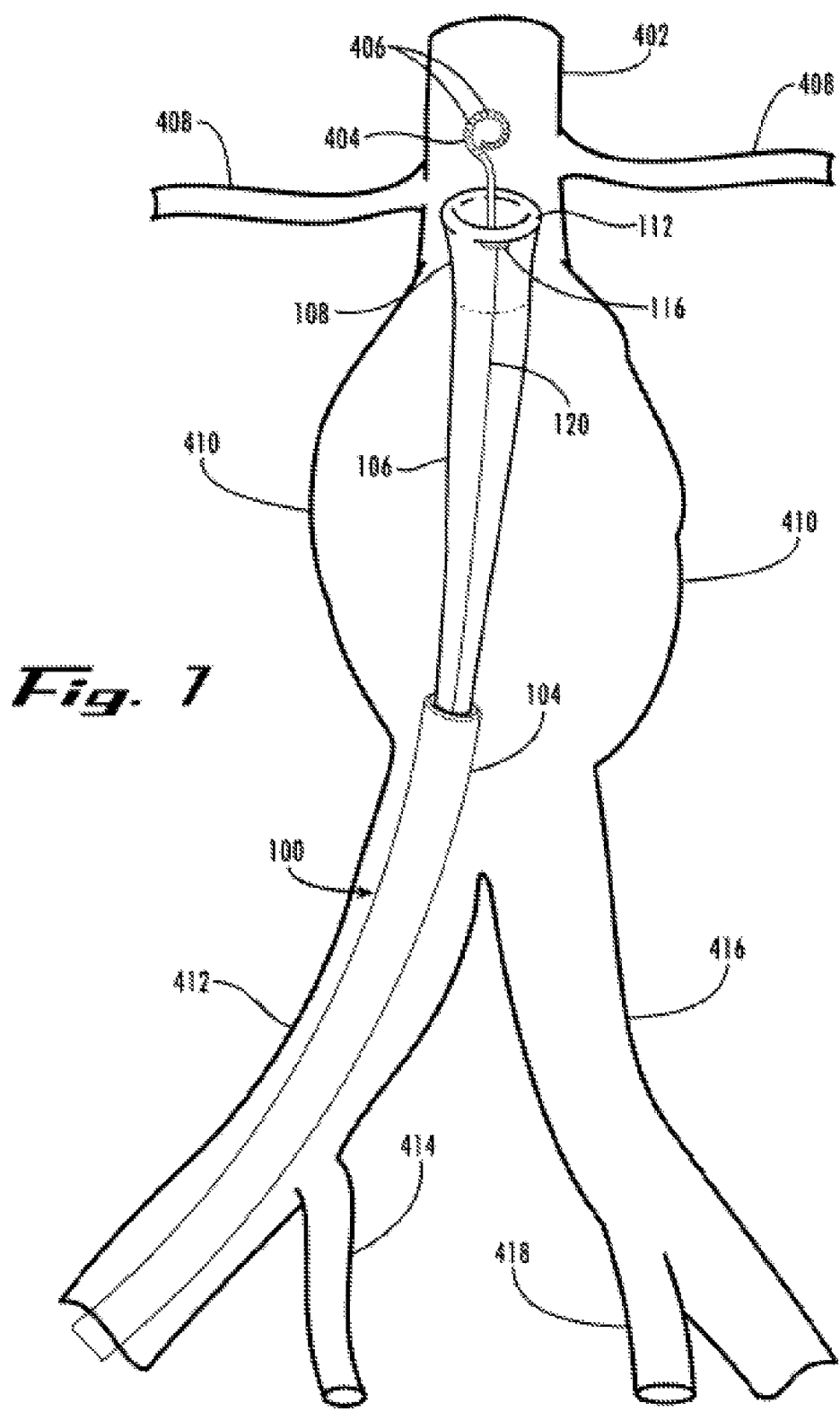
FIG. 7 is a perspective anatomic view of the disclosed embodiment of the present invention of FIG. 6 in which the implant delivery catheter has been slightly withdrawn under radiographic control to position the proximal tip of the implant distal to the origins of the renal arteries to preserve flow therein.

FIG. 7 is a continuation of the disclosed embodiment of the present invention of FIG. 6 in which the level of the proximal circumferential sealable collar 112 has been adjusted by the operator with respect to the level of the renal arteries 408 for optimal deployment.

Figure 8:
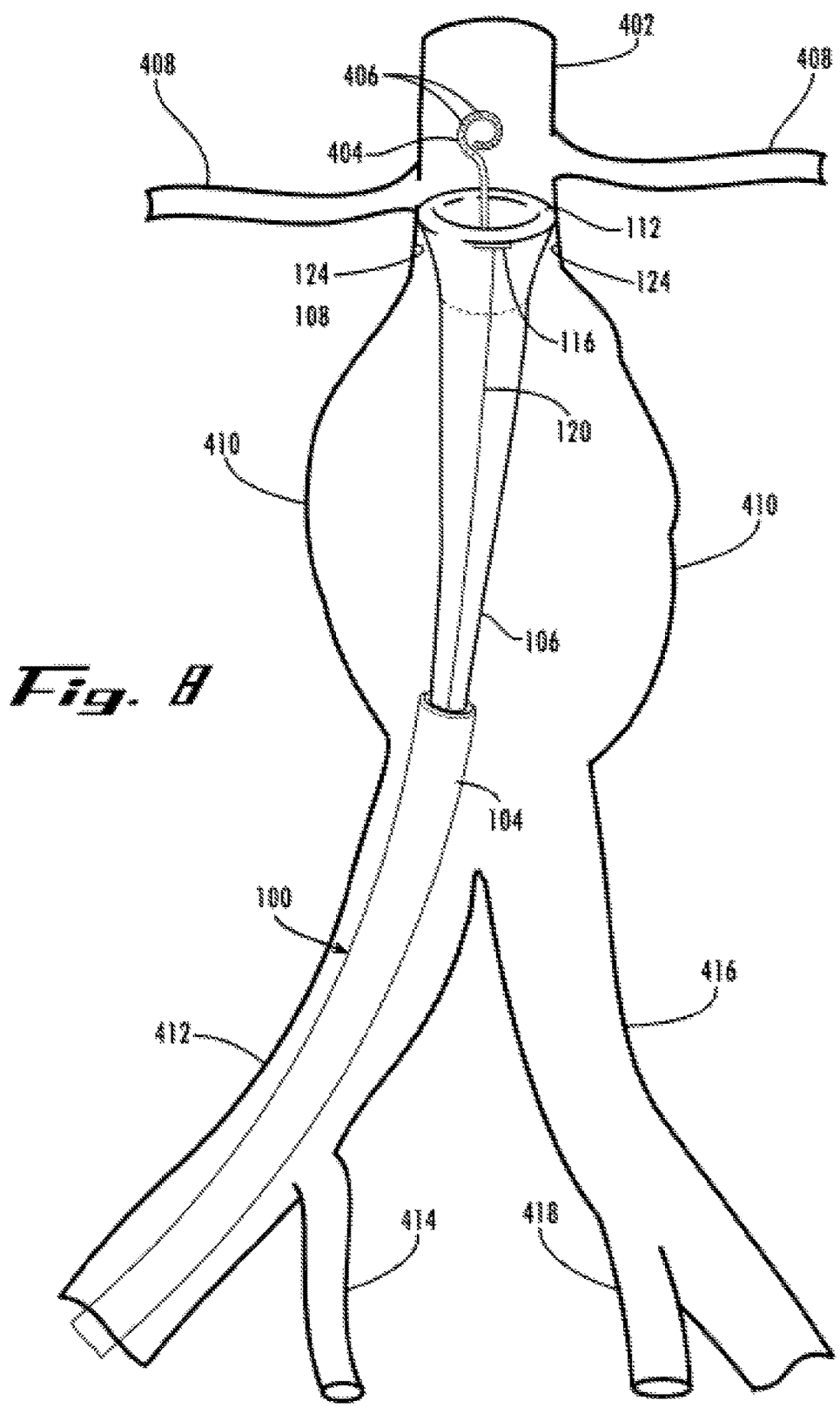
FIG. 8 is a perspective anatomic view of the disclosed embodiment of the present invention of FIG. 7 in which operator action on one or more control leads connected to one or more variable sealing devices has caused the extended circumferential sealable collar of the implant's elastic proximal end to firmly and fully contact the inner wall of the aorta, effecting a vascular seal therein.

FIG. 8 is a continuation of the disclosed embodiment of the present invention of FIG. 7 in which operator action on one or more proximal control leads 120 connected to one or more proximal variable sealing devices 116 has caused the proximal circumferential sealable collar 112 of the elastic proximal end 108 of the endovascular implant 200 to firmly and fully contact the aortic inner wall 124, effecting a vascular seal therein.

Figure 9:
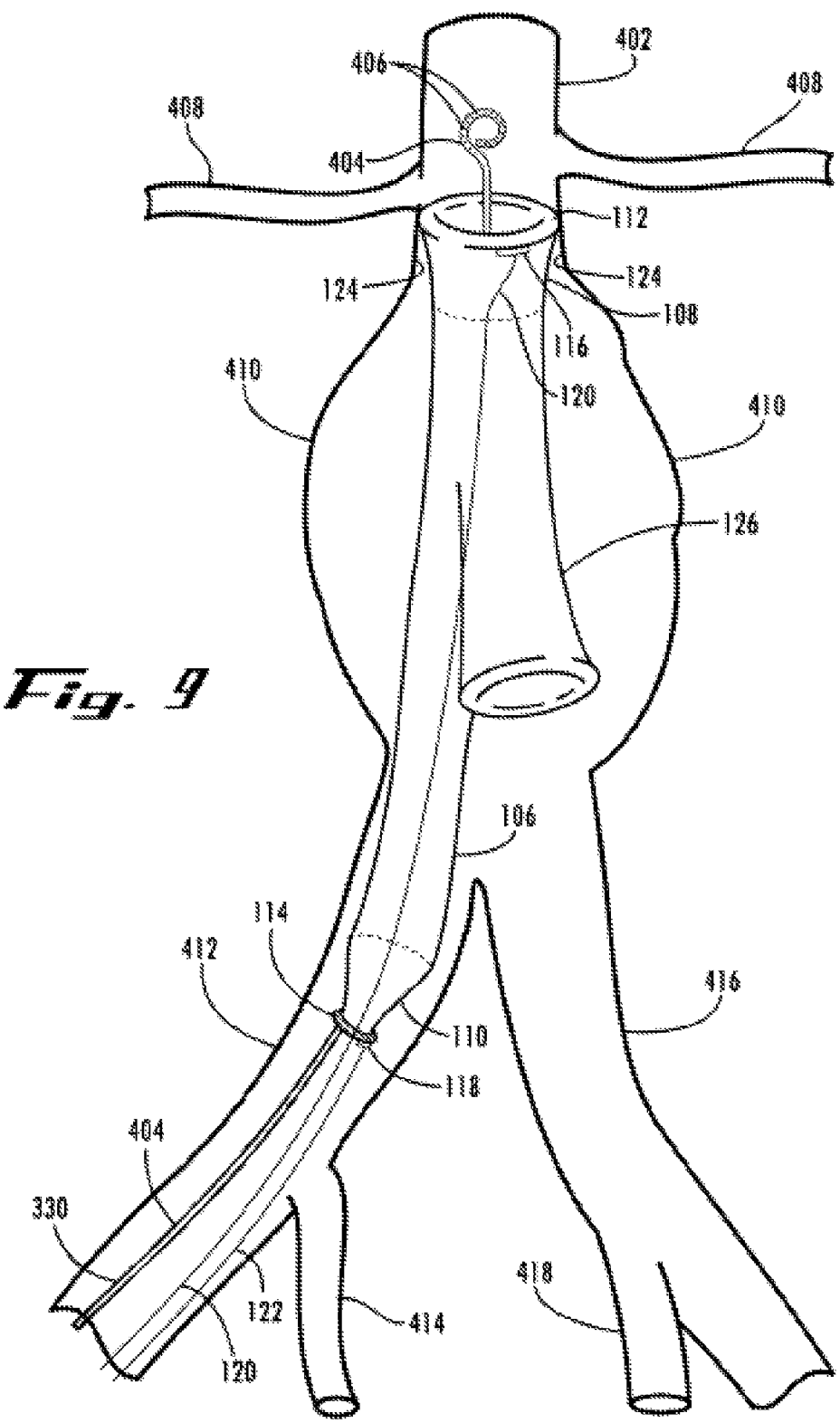
FIG. 9 is a perspective anatomic view of the disclosed embodiment of the present invention of FIG. 8 in which operator action has fully retracted or opened and removed the sheath of the implant delivery catheter allowing the endograft implant therein to fully decompress or unfold, to expose a distal elastic implant end and a non-elastic contralateral cuff.

FIG. 9 is a continuation of the disclosed embodiment of the present invention of FIG. 8 in which operator action has fully retracted or opened and removed the main implant delivery sheath 104 of the main implant delivery catheter 100 allowing the endovascular implant 200 therein to fully decompress or unfold, thus exposing a distal elastic implant end 110 and a non-elastic contralateral cuff 126. At this point in a deployment procedure, additional contrast dye injection would likely again be performed to ascertain that there is a complete seal at the level of the proximal circumferential sealable collar 112. If leakage is still visualized, additional operator action on the proximal control lead (s) 120 may be used to further expand the proximal circumferential sealable collar 112 to secure an acceptable seal. Alternately, operator action may reduce the expanded proximal circumferential sealable collar 112 to allow its reposition and redeployment, again under real-time radiographic or other visualized control.

Figure 10:
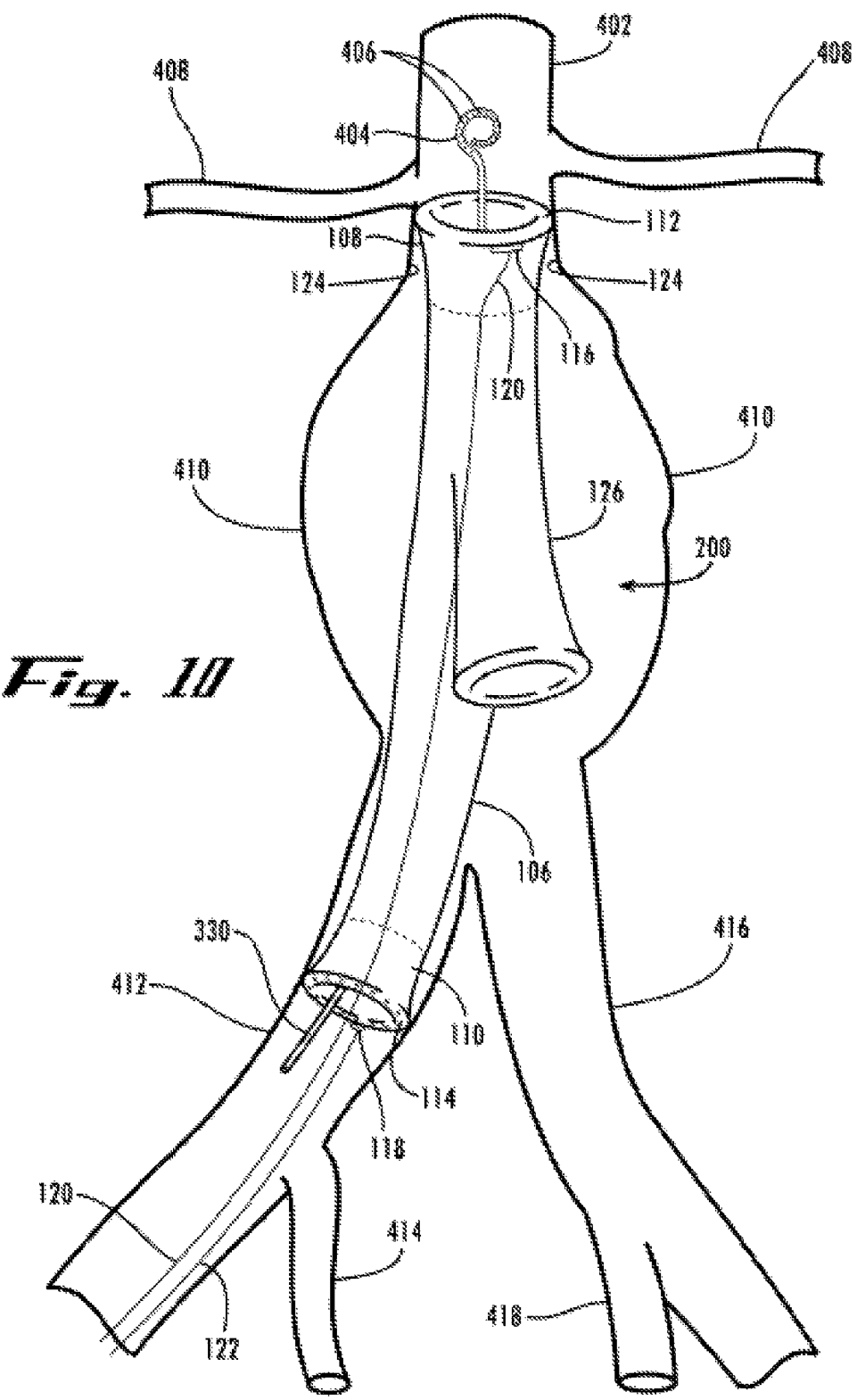
FIG. 10 is a perspective anatomic view of the disclosed embodiment of the present invention of FIG. 9 in which operator action on one or more control leads connected to one or more variable sealing devices has caused the extended circumferential sealable collar of the implant's elastic distal end to firmly and fully contact the inner wall of the common iliac artery above the origin of the internal iliac artery, effecting a vascular seal therein and preserving flow through the internal iliac artery.

FIG. 10 is a continuation of the disclosed embodiment of the present invention of FIG. 9 once a suitable proximal seal has been achieved. Operator action on one or more distal control leads 122 connected to one or more distal variable sealing devices 118 has caused the extended distal circumferential sealable collar 114 of the endovascular implant's 200 elastic distal end 110 to firmly and fully contact the inner wall of the common iliac artery 412 above the origin of the internal iliac artery 414, effecting a vascular seal therein and preserving flow through the internal iliac artery 414. Additional contrast dye injection through the injector cannula 404 would be used by the operator to confirm adequate seals both proximally and distally at this point.

Figure 11:
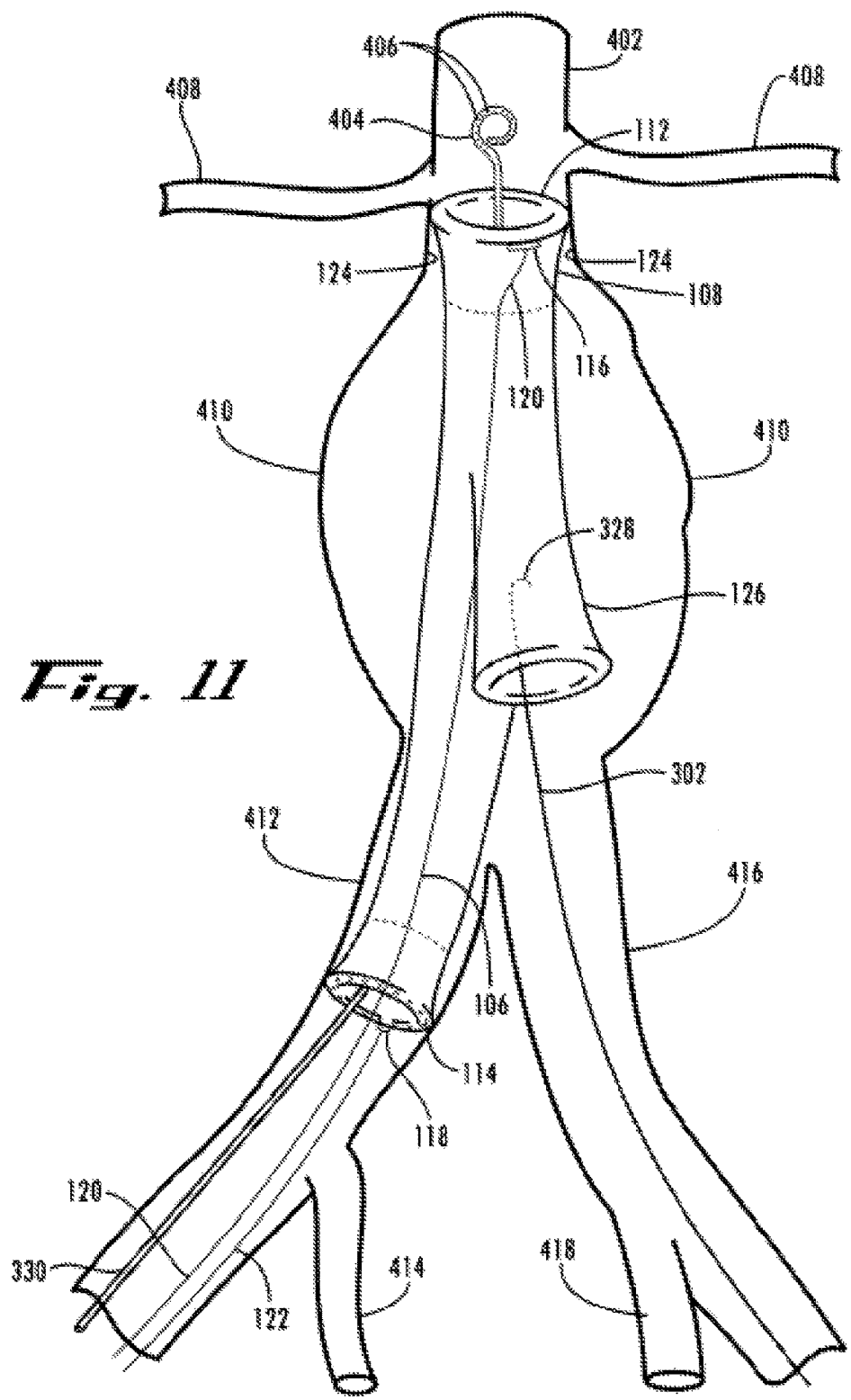
FIG. 11 is a perspective anatomic view of the disclosed embodiment of the present invention of FIG. 10 in which operator action has placed a hooked second guide wire to grasp and stabilize the non-elastic contralateral cuff under radiographic visualization through an access via a second side through a femoral artery.

FIG. 11 is a continuation of the disclosed embodiment of the present invention of FIG. 10 in which operator action has placed a second guide wire 302 provided with an engagement tip 328 to grasp and stabilize the non-elastic contralateral cuff 126 under radiographic or other imaging control through an access via a second side through a femoral arteriotomy (not shown in FIG. 11).

Figure 12:
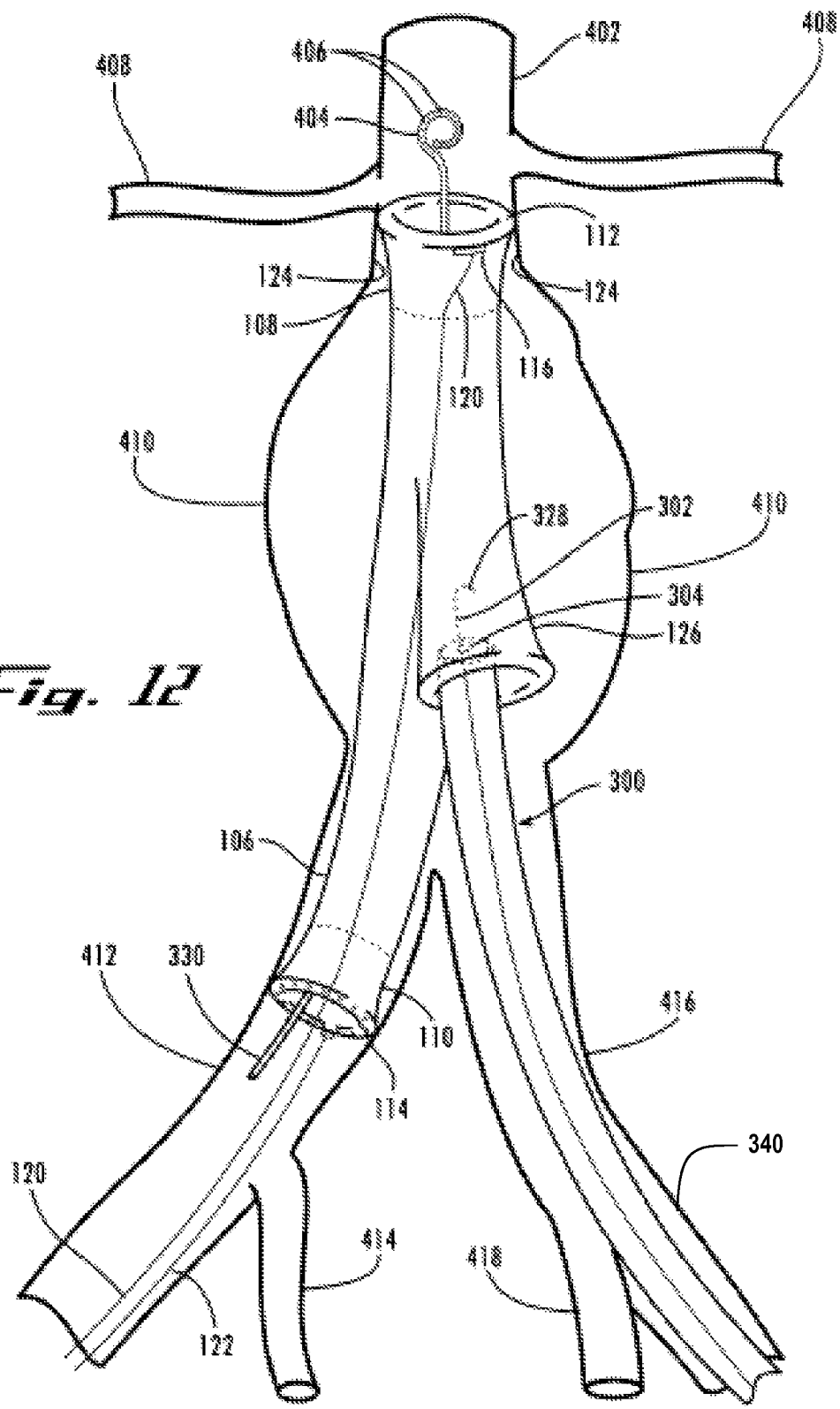
FIG. 12 is a perspective anatomic view of the disclosed embodiment of the present invention of FIG. 11 in which operator action has placed a contralateral delivery catheter over the second guide wire.

FIG. 12 is a continuation of the disclosed embodiment of the present invention of FIG. 11 in which operator action has placed a contralateral delivery catheter 300 over the second guide wire 302. The contralateral delivery catheter 300 includes a contralateral delivery catheter lumen 304 and a contralateral delivery catheter sheath 340 which may be operably opened or retracted by operator action.

Figure 13:
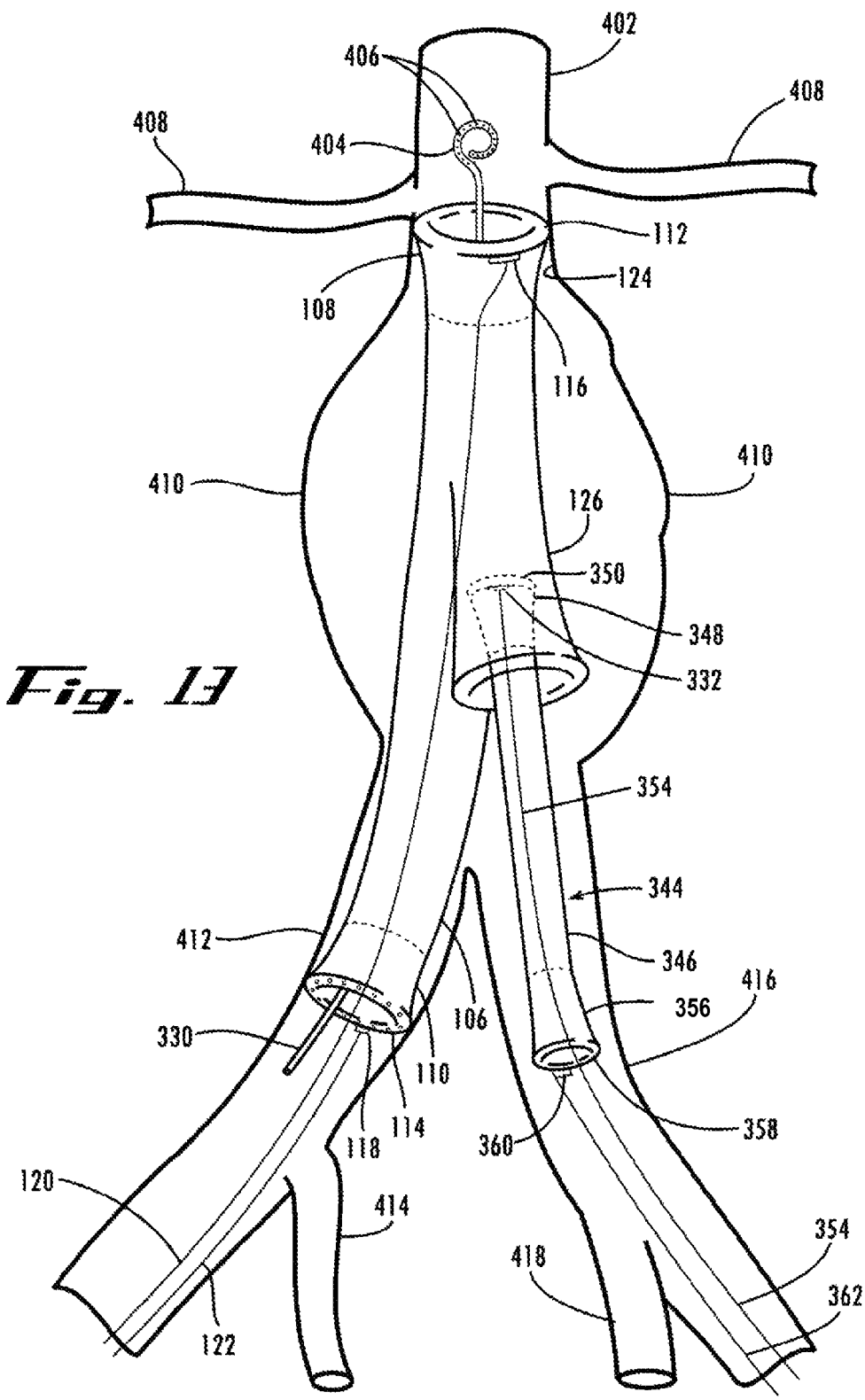
FIG. 13 is a perspective anatomic view of the disclosed embodiment of the present invention of FIG. 12 in which operator action has removed the sheath of the contralateral delivery catheter allowing the endograft segmental implant therein to fully decompress or unfold, to expose a proximal segmental elastic implant end, a distal segmental elastic implant end, and the full length of the non-elastic segmental tubular implant body connecting said ends.

FIG. 13 is a continuation of the disclosed embodiment of the present invention of FIG. 12 in which operator action has removed the contralateral delivery catheter sheath 340 of the contralateral delivery catheter 300 allowing the endograft segmental implant 344 therein to fully decompress or unfold to expose a proximal segmental elastic implant end 348, a distal segmental elastic implant end 356, and the full length of a non-elastic segmental tubular implant body 346 connecting said ends 348 and 356.

Figure 14:
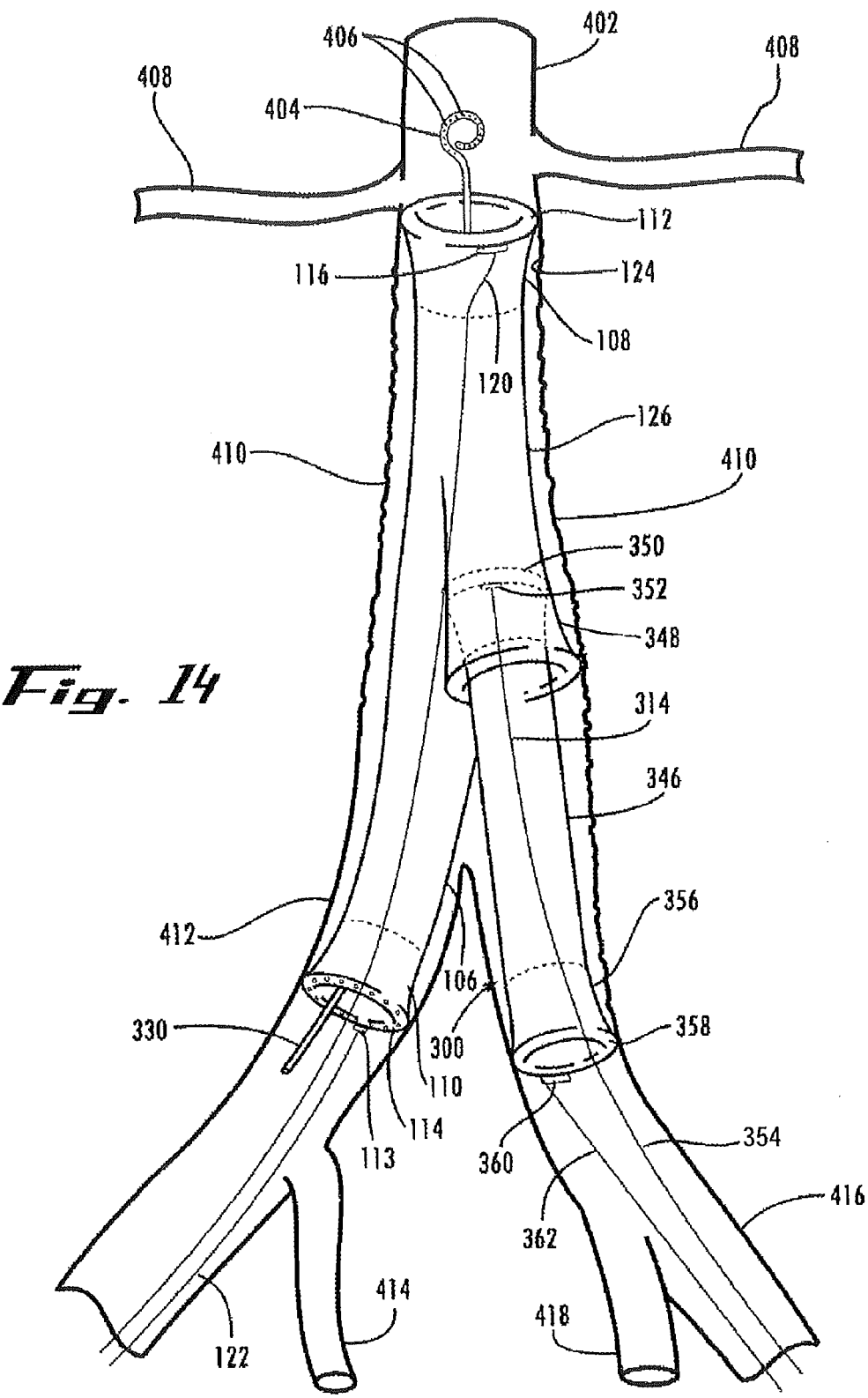
FIG. 14 is a perspective anatomic view of the disclosed embodiment of the present invention of FIG. 13 in which operator action on one or more control leads connected to one or more variable sealing devices has caused the extended circumferential sealable collar of the implant's proximal segmental elastic implant end to expand to firmly and fully contact the inner walls of the non-elastic contralateral cuff effecting a proximal seal, and then similarly caused the extended circumferential sealable collar of the implant's distal segmental elastic implant end to expand to firmly and fully contact the inner wall of the common iliac artery on the second side above the origin of the internal iliac artery, effecting a vascular seal therein and preserving flow through the internal iliac artery.

FIG. 14 is a continuation of the disclosed embodiment of the present invention of FIG. 13 in which operator action on one or more proximal segmental control leads 354 connected to one or more proximal segmental variable sealing devices 352 has caused the expansion of proximal segmental circumferential sealable collar 350 of the endograft segmental implant's 344 elastic proximal segmental implant end 348 to firmly and fully contact the inner walls of the non-elastic contralateral cuff 126 effecting a proximal seal, and then similarly caused the distal segmental circumferential sealable collar 358 of the endograft segmental implant's 344 elastic distal segmental implant end 356 to expand to firmly and fully contact the inner wall of the common iliac artery 416 on the second side above the origin of the internal iliac artery 418, effecting a vascular seal therein and preserving flow through the internal iliac artery 418. Once sealed, the aortic aneurysmal sac 410 is devascularized and collapses.

Figure 15:
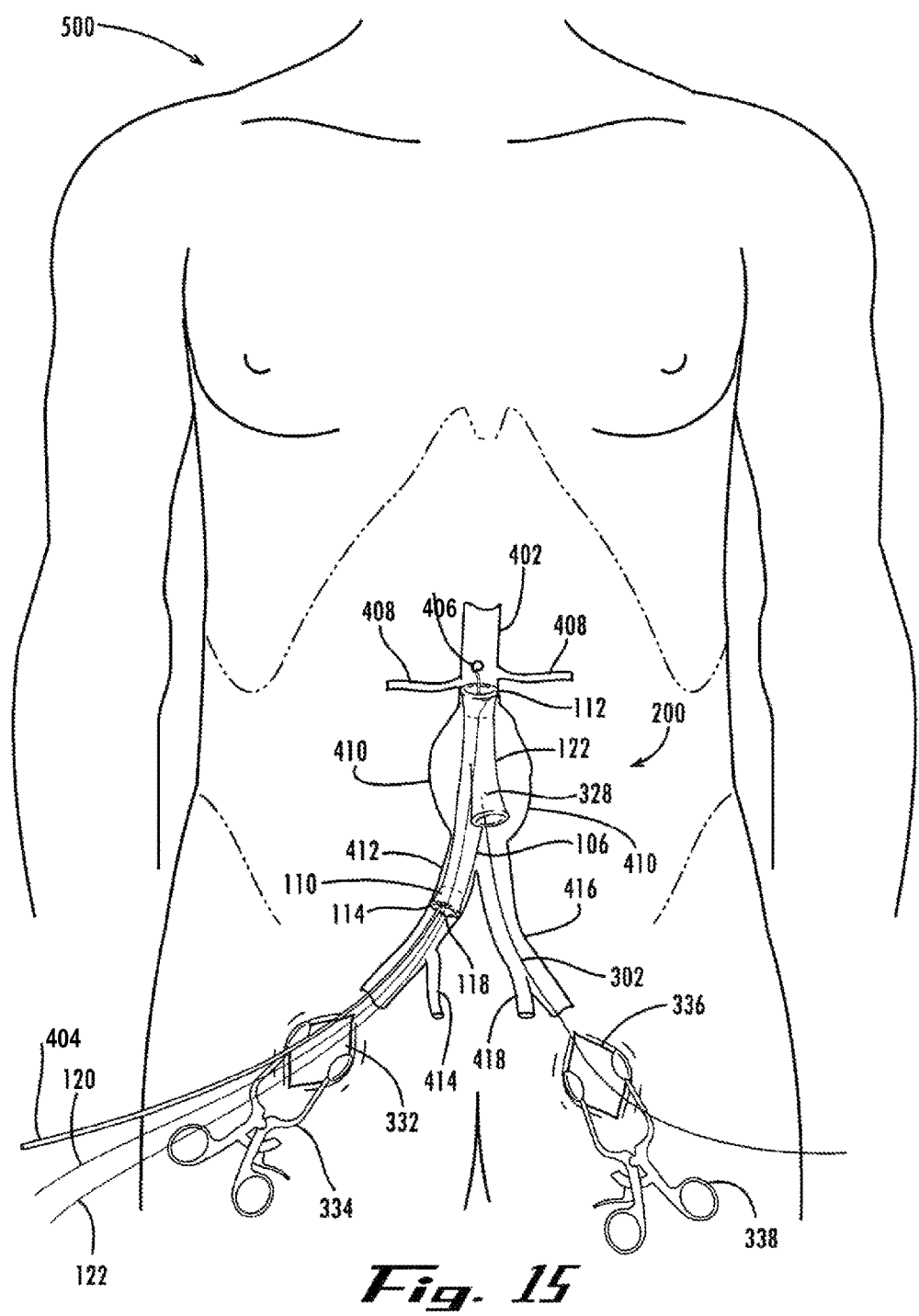
FIG. 15 shows an diagrammatic view of a patient in a dorsal supine position, with a disclosed embodiment of an endovascular implant according to the present invention in sealed position in the patient's abdominal aorta proximally and distally, and with arteriotomy incisions in both femoral arteries with an injector cannula and proximal and distal control leads in place in the patient's right arteriotomy site for radiographic contrast dye injection and a second guide wire in place in the patient's left arteriotomy site, corresponding to the procedural stage shown in FIG. 11.

FIG. 15 shows a diagrammatic view of a patient 500 in a dorsal supine position, with a disclosed embodiment of an endovascular implant 200 according to the present invention in sealed position in the patient's abdominal aorta 402 proximally and distally, and with arteriotomy incisions 332, 336 in both femoral arteries with an injector cannula 404 for radiographic contrast dye injection and proximal 120 and distal 122 control leads for operator manipulation in place in the patient's right arteriotomy site 332 and a second guide wire 302 in place in the patient's left arteriotomy site 336, corresponding to the procedural stage shown in FIG. 11.

Figure 16:
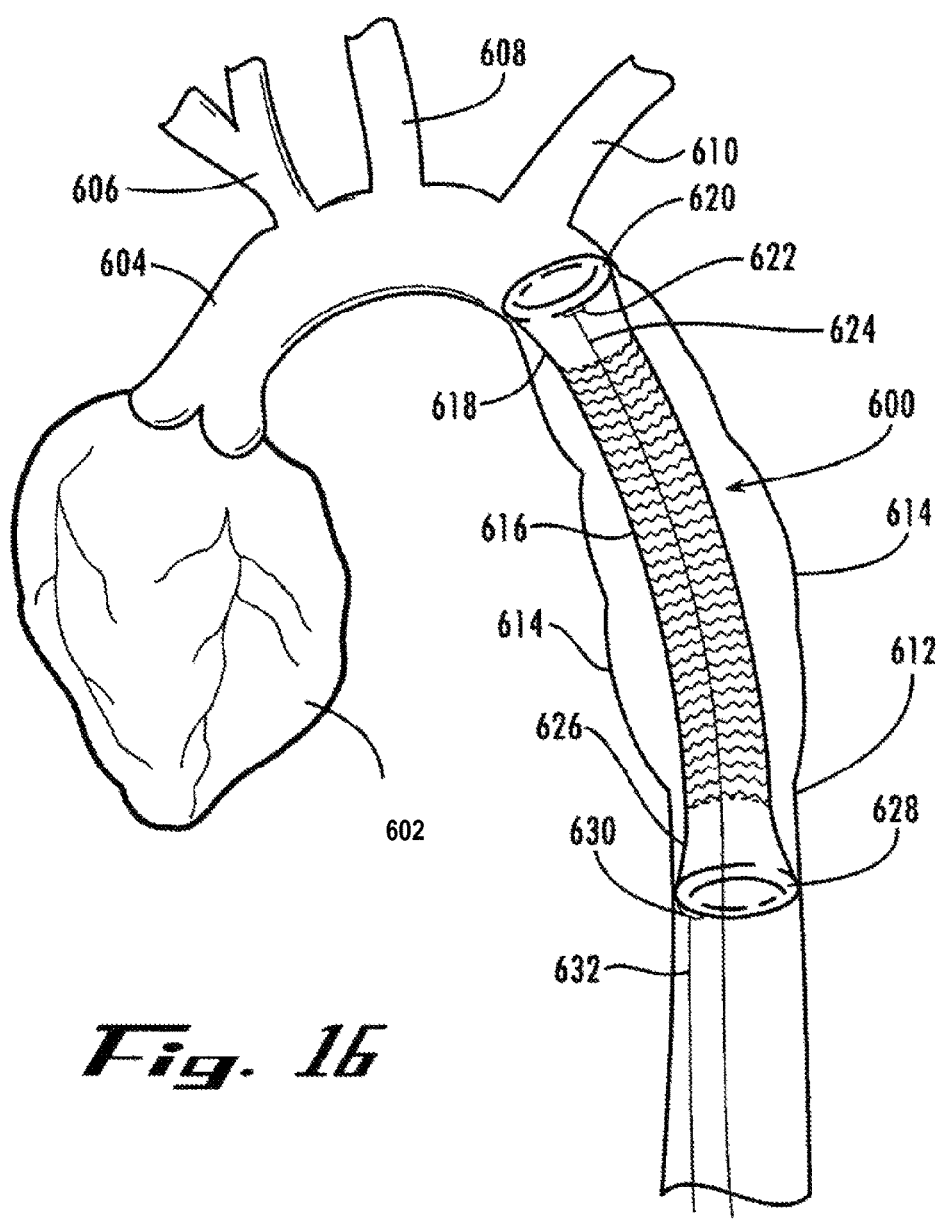
FIG. 16 is a longitudinal anatomic view showing a disclosed embodiment of a thoracic endovascular implant according to the present invention in sealed position proximally and distally in a patient's descending thoracic aorta.

FIG. 16 shows an anatomic view of a disclosed embodiment of a thoracic endovascular implant 600 according to the present invention in sealed position proximally and distally in a patient's descending thoracic aorta 612, traversing a devascularized thoracic aortic aneurysm 614. In a patient, the ascending aorta 604 arises from the heart 602 and gives rise to the innominate artery 606, the left common carotid artery 608, and the left subclavian artery 610 before continuing as the descending thoracic aorta 612. The thoracic endovascular implant 600 includes a non-elastic tubular thoracic implant body 616 with an elastic proximal thoracic end 618 and an elastic distal thoracic end 626. The elastic proximal thoracic end 618 terminates in a proximal thoracic sealable circumferential collar 620, controlled by a proximal thoracic variable sealing device 622 which is operated by a proximal thoracic control lead 624 that traverses a thoracic implant delivery catheter (not shown in FIG. 16) and exits distally for interface with an operator (not shown in FIG. 16). The elastic distal thoracic end 626 terminates in a distal sealable thoracic circumferential collar 628, controlled by a distal thoracic variable sealing device 630 which is operated by a distal thoracic control lead 632 that exits a thoracic implant delivery catheter distally for interface with an operator (not shown in FIG. 6).

Figure 17:
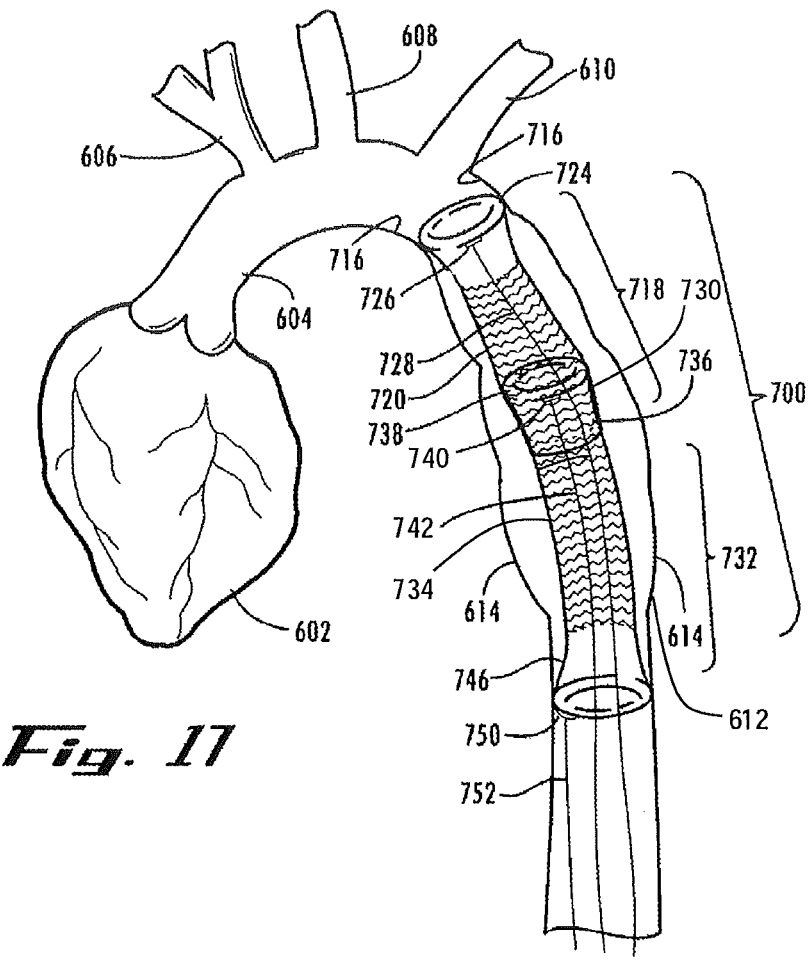
FIG. 17 is a longitudinal anatomic view showing an alternate disclosed embodiment of a thoracic endovascular implant in a patient's descending thoracic aorta according to the present invention in which a first thoracic endovascular implant with a non-elastic distal cuff has been sealed in position proximally and distally has been joined by a second thoracic endovascular implant with a non-elastic tubular body with an elastic proximal end and an elastic distal end, both containing circumferential sealable collars and variable sealing devices capable of achieving a desired seal between the collar and the vessel's inner wall.

FIG. 17 provides an anatomic view showing an alternate disclosed embodiment of a thoracic endovascular implant 700 in a patient's descending thoracic aorta 612 according to the present invention in which a first thoracic endovascular implant 718 includes a non-elastic distal cuff 730, a proximal first thoracic circumferential sealable collar 724, a proximal first thoracic variable sealing device 726, and a proximal first thoracic control lead 728. As shown in FIG. 17, the first thoracic endovascular implant 718 has been sealed in position proximally by operator action on the proximal first thoracic variable sealing device 726 using the proximal first thoracic control lead 728, expanding the proximal first thoracic circumferential sealable collar 724 to achieve a proximal seal within the descending thoracic aorta 612, and effectively devascularizing a thoracic aneurysm 614 therein.

As further shown in FIG. 17, the first thoracic endovascular implant 718 has been joined distally by a second thoracic endovascular implant 732, which includes an elastic proximal second thoracic implant end 736, a non-elastic tubular second thoracic implant body 734, and an elastic distal second thoracic implant end 746. The elastic proximal second thoracic implant end 736 includes a proximal second thoracic circumferential sealable collar 738, a proximal second thoracic variable sealing device 740, and a proximal second thoracic control lead 742, and the elastic distal second thoracic implant end 746 includes a distal second thoracic circumferential sealable collar 748, a distal second thoracic variable sealing device 750, and a distal second thoracic control lead 752.

In an exemplary application according to the present invention as shown in FIG. 17, an operator would first secure a seal in the proximal descending thoracic aorta using the first thoracic endovascular implant 718, and then seal the proximal and distal aspects, respectively, of the second thoracic endovascular implant 732, using real-time radiographic or other visualization techniques with injected contrast dye as previously described in this disclosure.

Figure 18A:
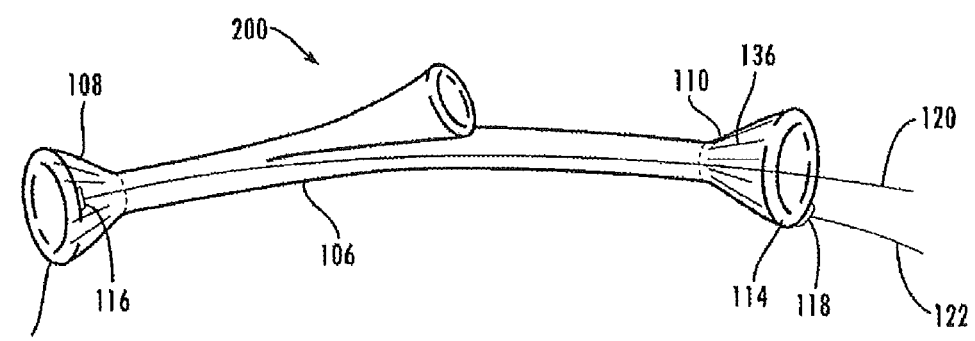
FIG. 18A is a side perspective view of the disclosed embodiment of an endovascular implant according to the present invention in which the proximal and distal circumferential sealable collars are provided with retractable retention tines and shown in a retracted, pre-deployment position.
Figure 18B:
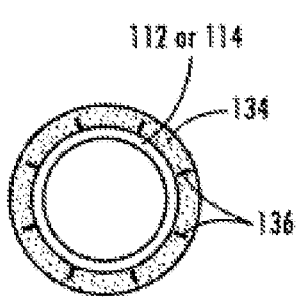
FIG. 18B is a cross-sectional view of a disclosed embodiment according to the present invention of a proximal or distal circumferential sealable implant collar with retention tines covered by a compressible foam sheathing in a retracted, pre-deployment position.

FIGS. 18A and 18B show an embodiment of an endovascular implant according to the present invention similar to the disclosure of FIG. 1B, with the additional inclusion of one of more retention tines 136 attached to the proximal circumferential sealable collar 112 and distal circumferential sealable collar 114.

In a preferred embodiment according to the present invention, a plurality of retention tines 136 is used. In a preferred embodiment according to the present invention, the retention tines 136 are oriented to extend radially outward from the proximal circumferential sealable collar 112 and distal circumferential sealable collar 114. In various preferred embodiment according to the present invention, the retention tines 136 may be oriented to extend perpendicularly or at any other desired angle outward from the proximal circumferential sealable collar 112 and distal circumferential sealable collar 114.

In various preferred embodiment according to the present invention, the retention tines 136 may be constructed of any biocompatible material including, but not limited to, metals, plastics, or ceramics.

As further shown in FIG. 18B the retention tines 136 of the proximal circumferential sealable collar 112 and distal circumferential sealable collar 114 covered by a compressible foam sheathing 134 in a pre-deployment position. In various preferred embodiment according to the present invention, the compressible foam sheathing 134 may be constructed of any biocompatible material of suitable compressibility to allow the foam to be substantially compressed by the pressure of the proximal circumferential sealable collar 112 and distal circumferential sealable collar 114 against the inner wall of a target artery, upon operator deployment. The compressible foam sheathing 134 may also be constructed of material of suitable memory characteristics to allow the foam to substantially decompress to its pre-deployment position, covering the retention tines 136, if pressure against the arterial wall is removed, thus allowing repositioning or removal of an endovascular implant according to the present invention at the operator's discretion.

Compressible foam sheathing 134 may be any biocompatible foam material of either an open or closed cell structure with sufficient compressibility and resilience to allow rapid recovery in a non-compressed state. In various preferred embodiments according to the present invention, such foam materials may be viscoelastic foam with a compressible cellular material that has both elastic (spring-like) and viscous (time-dependent) properties. Viscoelastic foam differs from regular foam by having time-dependent behaviors such as creep, stress relaxation, and hysteresis.

Figure 19B:
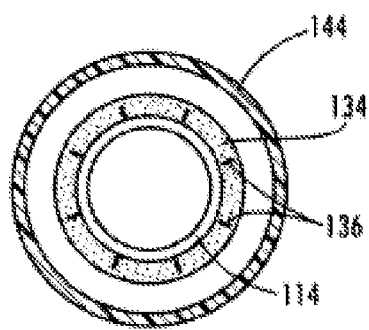
FIG. 19B is a cross-sectional view of the distal circumferential sealable implant collar in FIG. 19A, showing the compressible foam sheathing covering the collar's retention tines within a vessel's lumen.
Figure 19A:
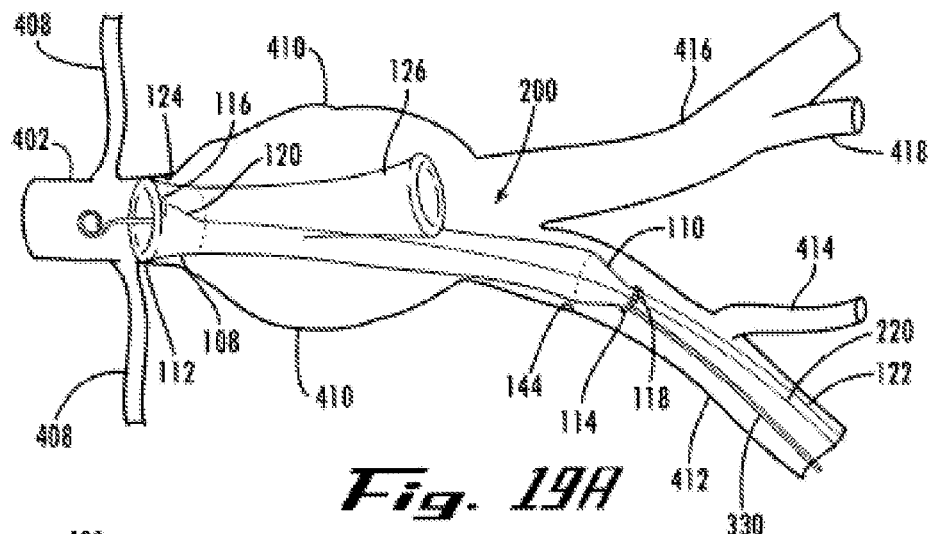
FIG. 19A is a longitudinal anatomic view of a disclosed embodiment according to the present invention of an endovascular implant which is being deployed and sealed proximally in an abdominal aorta containing an infrarenal aneurysm, with incomplete distal circumferential sealable implant collar expansion and seal at this stage of the procedure.

FIGS. 19A and 19B show the exemplary endovascular implant of FIGS. 18A and 18B in the anatomic context of an endovascular implant 200 being deployed and sealed proximally in an abdominal aorta 402 containing an aneurysm 410, with complete expansion and seal at the level of the proximal circumferential sealable implant collar 112 against the aortic inner wall 124, but incomplete expansion and no seal against the arterial inner wall 144 at the level of the distal circumferential sealable implant collar 114 at this stage of the procedure. As shown in the cross-sectional view of FIG. 19B, the retention tines 136 of the proximal circumferential sealable collar 112 and distal circumferential sealable collar 114 are covered by a compressible foam sheathing 134 in a pre-deployment position.

Figure 20A:
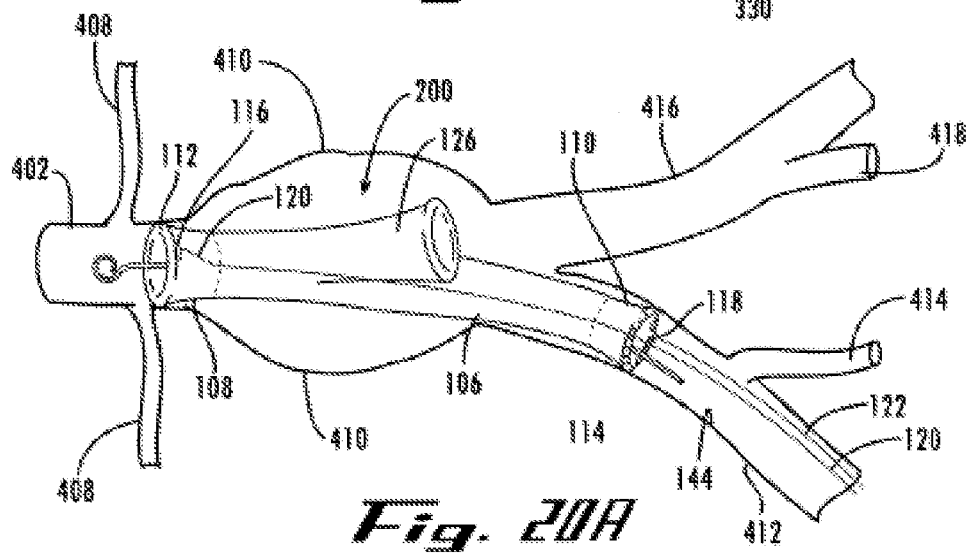
FIG. 20A is a longitudinal anatomic view of a disclosed embodiment according to the present invention of an endovascular implant which is being deployed and sealed proximally in an abdominal aorta containing an infrarenal aneurysm, with complete proximal circumferential sealable implant collar expansion and seal at this stage of the procedure.
Figure 20B:
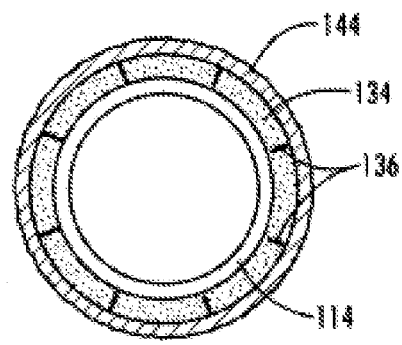
FIG. 20B is a cross-sectional view of the proximal circumferential sealable implant collar in FIG. 20A, showing compression of the compressible foam sheathing allowing the collar's retention tines to contact and engage the aortic wall circumferentially.

FIGS. 20A and 20B further show the exemplary endovascular implant of FIGS. 18A and 18B in the anatomic context of an endovascular implant 200 being deployed and sealed proximally in an abdominal aorta 402 containing an aneurysm 410, now with complete expansion of the distal circumferential sealable implant collar 114 and complete seal against the arterial inner wall 144 at this stage of the procedure. As shown in the cross-sectional view of FIG. 20B, compressible foam sheathing 134 is compressed between the distal circumferential sealable collar 114 and the arterial inner wall 144, allowing the retention tines 136 to engage the arterial inner wall 144 in their deployed position, thereby serving to retain the deployed position of the endovascular implant 200.

In given various preferred embodiments according to the present invention, retention tines 136 and the compressible foam sheathing 134 as described above may be used in conjunction with any or all circumferentially sealable elements in this disclosure, including but not limited to, proximal circumferential sealable collars 112, distal circumferential sealable collars 114, proximal segmental circumferential sealable collars 314, distal segmental circumferential sealable collars 316, proximal thoracic circumferential sealable collars 620, distal thoracic circumferential sealable collars 628, proximal first thoracic circumferential sealable collars 724, proximal second thoracic circumferential sealable collars 738, and distal second thoracic circumferential sealable collars 748.

FIGS. 21 A-D illustrate details of an embodiment of a variable sealing device according to the present invention. A variable sealing mechanism assembly 2100 comprises a sealing device housing 2102 attached to a sealer belt 2104 with a sealer belt fixed end 2108 attached to said housing 2102 and with a sealer belt moveable end 2110 operably passing through said housing and collecting in a concentric belt receiver channel 2130 as said sealer belt moveable end 2110 exits said housing 2102. The sealer belt moveable end 2110 contains a plurality of uniformly distributed belt engagement slots 2106. The belt engagement slots 2106 may be round, oval, square, rectangular, triangular, or any other shape, but are sized, spaced, and configured on said sealer belt moveable end 2110 to engage with sealer gear teeth 2116 of a sealer gear 2114 rotatably located within a housing gear recess 2112 contained within said housing 2102. The sealer gear teeth 2116 are oriented to present on the outer circumference of said sealer gear 2114. On the inner circumference of said sealer gear 2114, a plurality of uniformly distributed sealer gear retainment slots 2118 are configured to receive a locking member 2120. The locking member 2120, in various embodiments according to the present invention may be a simple strip or bar as shown in FIGS. 21 A-D, or it may be triangular, cross-shaped, stellate or other geometric shapes that would allow the sealer gear retainment slots 2118 to receive the ends of said locking member 2120. The locking member 2120 is fabricated of a metal or plastic with resilient spring-like properties, such that, when depressed or pulled in a perpendicular vector with respect to the sealer gear 2114, the ends of said locking member 2120 are withdrawn from the sealer gear retainment slots 2118, thus allowing the sealer gear 2114 to rotate within said housing gear recess 2112, as shown in FIGS. 21 B and C. The locking member 2120 is further provided with one or more sealer gear drive pins 2126, which are received in gear drive pin slots 2128 of said sealer gear 2114 when the locking member 2120 is depressed, as shown in FIG. 21C. In various preferred embodiments according to the present invention, the gear drive pins 2126 and the gear drive pin slots 2128 may be tapered, straight, or otherwise shaped to facilitate their secure engagement and release. The locking member 2120 is depressed by action of a control lead shaft 2124, which is removably attached to the locking member 2120 at a control lead attachment 2122. In an exemplary embodiment of the present invention, as shown in FIG. 21C, while the locking member 2120 is released from the gear drive pin slots 2128 by a depressing action of the control lead shaft 2124, rotation of the control lead shaft 2124 will permit the sealer gear drive pins 2126 to transmit a rotational force to the sealer gear 2114, engaging the belt engagement slots 2106 in the movable end of the sealer belt 2110, and causing the movable end of the sealer belt 2110 to move in or out of the concentric belt receiver channel 2130. This motion has the effect of increasing or decreasing the surface area of the sealer belt 2104.

Figure 21A:
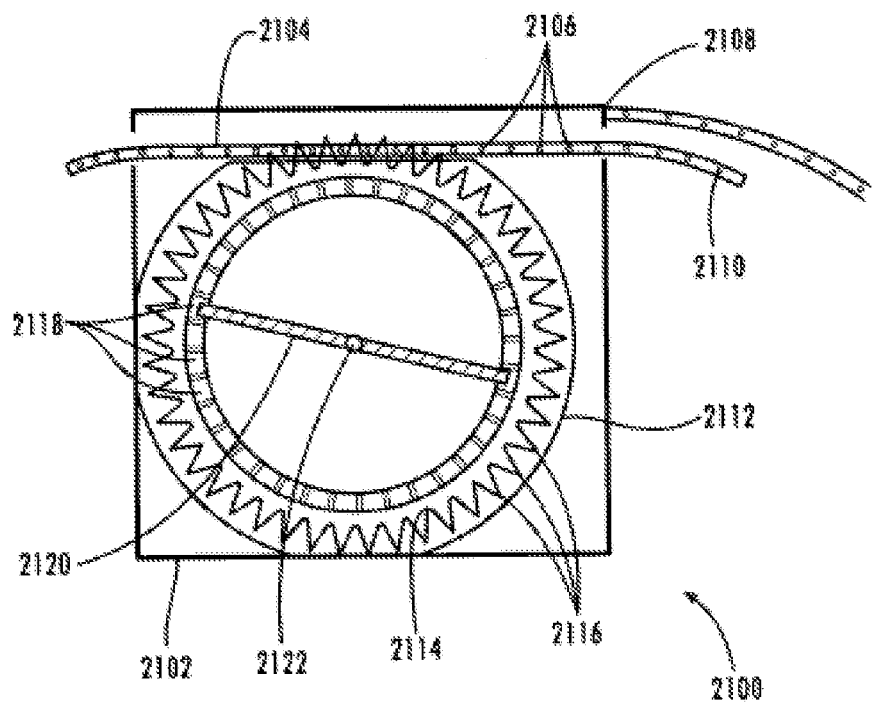
FIG. 21A is a perspective view of an embodiment of a variable sealing device according to the present invention.
Figure 21B:
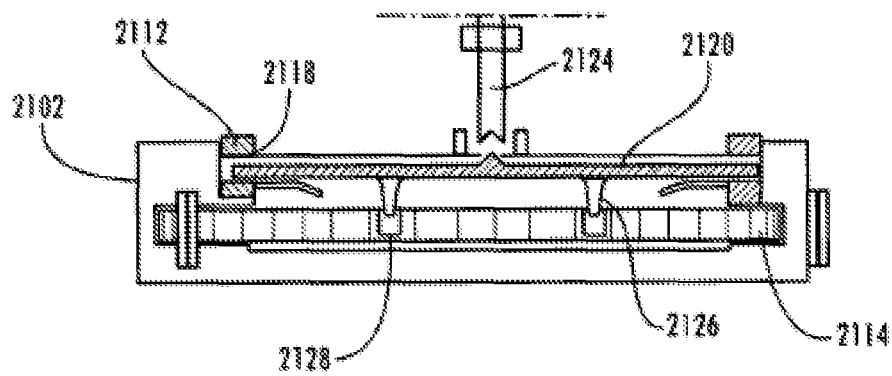
FIG. 21B is a sectional view of an embodiment of a variable sealing device according to the present invention, in which the mechanism is in a released, locked state.
Figure 21C:
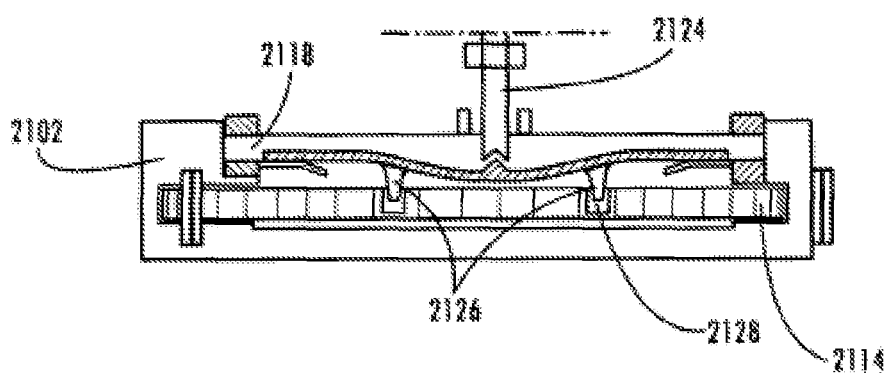
FIG. 21C is a sectional view of an embodiment of a variable sealing device according to the present invention, in which the mechanism is in an engaged, unlocked state.
Figure 21D:
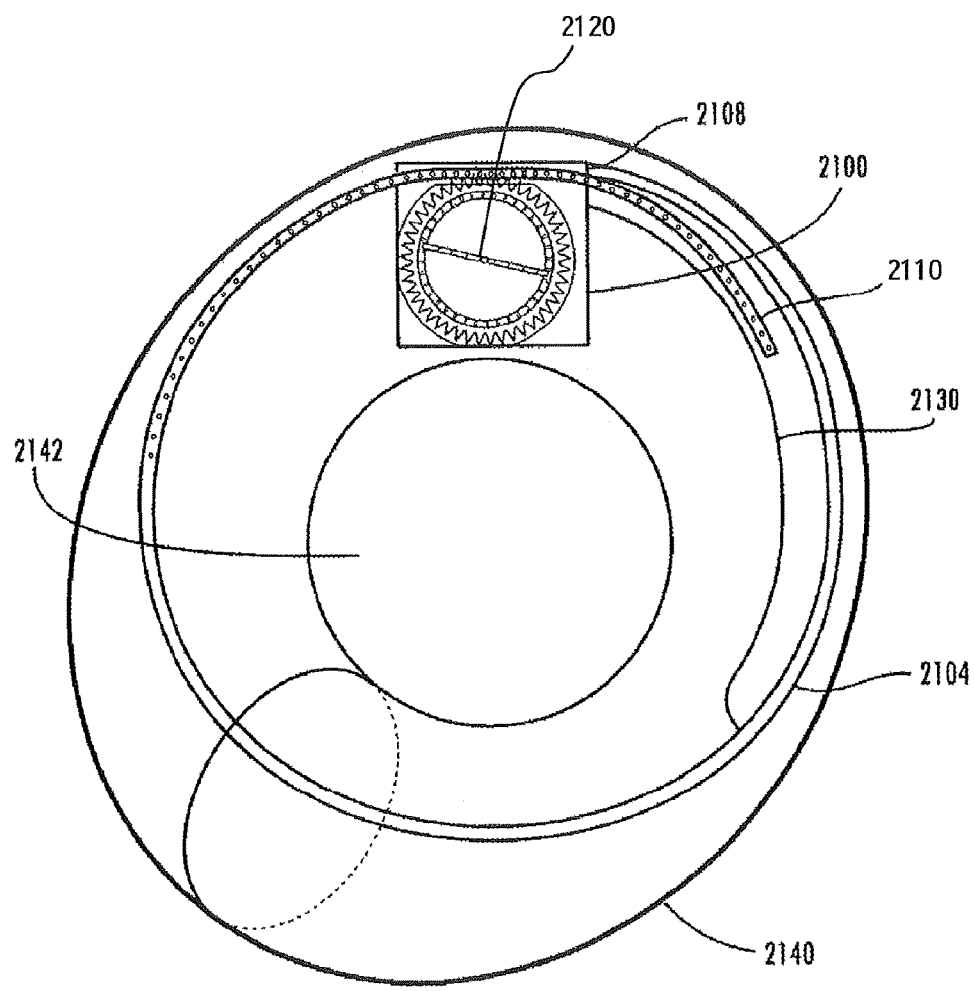
FIG. 21D is a perspective view of an embodiment of a sealable collar containing a variable sealing device according to the present invention.

FIG. 21D shows an exemplary embodiment according to the present invention, in which a sealable collar 2140 contains a variable sealing mechanism assembly 2100 comprising a sealing device housing 2102 attached to a sealer belt 2104 with a sealer belt fixed end 2108 attached to said housing 2102 and with a sealer belt moveable end 2110 operably passing through said housing and collecting in a concentric belt receiver channel 2130 as said sealer belt moveable end 2110 exits said housing 2102. The sealable collar 2140 is constructed of a tubular elastic body in a closed loop defining a central collar lumen 2142. The sealer belt 2104 may pass circumferentially through substantially all of the sealable collar 2140, as shown in FIG. 21D, but in alternate embodiments may pass through only some of the circumference of the sealable collar 2140. As the variable sealing mechanism assembly 2100 is operated, the length of the sealer belt 2104 may enlarge or constrict, with similar action on the sealable collar 2140, thus allowing a variable seal to be achieved between the sealable collar 2140 and the inner lumen of a vessel wall (not shown in FIG. 21D) containing the sealable collar 2140.

Within certain embodiments of the present invention, an endograft may also incorporate radio-opaque, echogenic materials and magnetic resonance imaging (MRI) responsive materials (i.e., MRI contrast agents) to aid in visualization of the device under x-ray, ultrasound, fluoroscopy MRI or other imaging modalities. In addition, various embodiments according to the present invention may incorporate markers comprising various radio-opaque, echogenic materials and magnetic resonance imaging (MRI) responsive materials that may be placed on the walls of an aneurysm sac or on other anatomic sites for improved postoperative visualization to monitor for aneurysmal revascularization.

As shown in FIGS. 22A-22F, various embodiments according to the present invention may also be provided with one or more endograft monitoring devices to facilitate diagnosis of postoperative graft failure and aneurysm revascularization. In some embodiments according to the present invention, endograft monitoring devices may be pressure sensors positioned to demonstrate positive pressure within the former aneurysmal sac in some manner that may be identifiable by electronic, radiographic, or other visual or electronic communications. FIGS. 22A-F illustrate yet other embodiments of endograft monitoring devices according to the present invention.

FIGS. 22A-22B show an embodiment of a sealable vascular endograft system 2200 which incorporates an endograft monitoring device comprising an radio-opaque graft attachment member 2205 joined at a monitoring pivot 2210 to a radio-opaque aneurysmal attachment 2220 which is affixed by an operator at the time of endograft placement to the inner wall of the aneurysmal sac 2215, which is shown in a collapsed, nonvascularized state in FIG. 22A, but in an expanded, revascularized state in FIG. 22B. As further shown in FIG. 22B, the expansion of the aneurysmal sac 2215, has the further effect of increasing the angle between the radio-opaque graft attachment member 2205 and the radio-opaque aneurysmal attachment 2220. In such an embodiment, plain radiographs or other visualization means could be employed to evaluate the angle between the attachment members of an endograft monitoring device to detect endograft failure and revascularization of the aneurysm without requiring more invasive and expensive diagnostic studies.

FIGS. 22C and 22D illustrate yet another embodiment of an embodiment of a sealable vascular endograft system 2200 which incorporates an endograft monitoring device comprising an radio-opaque graft attachment 2202 pivotably joined by two or more radio-opaque graft frame members 2212 which are in turn joined frame pivots 2204 to radio-opaque aneurysmal frame members 2214 which are joined at an aneurysmal attachment 2216 which is affixed by an operator at the time of endograft placement to the inner wall of the aneurysmal sac 2215, which is shown in a collapsed, nonvascularized state in FIG. 22C, but in an expanded, revascularized state in FIG. 22D. As further shown in FIG. 22D, the expansion of the aneurysmal sac 2215, has the further effect of increasing the angles between the radio-opaque graft frame member 2212 and the radio-opaque aneurysmal frame members 2214 to create a square or polygonal shape visible on radiographs. In such an embodiment, plain radiographs or other visualization means could again be employed to evaluate the angles between the attachment members of an endograft monitoring device to detect endograft failure and revascularization of the aneurysm without requiring more invasive and expensive diagnostic studies.

FIGS. 22E and 22F illustrate still another embodiment of an embodiment of a sealable vascular endograft system 2200 which incorporates an endograft monitoring device comprising two or more radio-opaque graft attachment 2202 pivotably joined by two or more radio-opaque graft frame members 2212 which are in turn joined frame pivots 2204 to radio-opaque aneurysmal frame members 2214 which are joined at two or more aneurysmal attachments 2216 which are affixed by an operator at the time of endograft placement to the inner wall of the aneurysmal sac 2215, which is shown in a collapsed, nonvascularized state in FIG. 22E, but in an expanded, revascularized state in FIG. 22F. As further shown in FIG. 22F, the expansion of the aneurysmal sac 2215, has the further effect of increasing the angles between the radio-opaque graft frame member 2212 and the radio-opaque aneurysmal frame members 2214 to create a square or polygonal shape visible on radiographs. In such an embodiment, three-dimensional, cage-like structures could be formed by the various frame members described, further enhancing the clinical visibility of an indication of aneurysmal revascularization.

Although the foregoing embodiments of the present invention have been described in some detail by way of illustration and example for purposes of clarity and understanding, it will be apparent to those skilled in the art that certain changes and modifications may be practiced within the spirit and scope of the present invention. Therefore, the description and examples presented herein should not be construed to limit the scope of the present invention, the essential features of which are set forth in the appended claims.

What is claimed is:

1. A sealable vascular endograft system for placement in a vascular defect, comprising:
   an elongated implant delivery catheter having a catheter proximal end and a catheter distal end and shaped to be disposed within a blood vessel having internal walls, the implant delivery catheter including:
      an implant delivery catheter sheath defining an implant delivery catheter lumen; and
      an endovascular implant removably disposed within the implant delivery catheter lumen in a compressed or folded state for delivery thereof to the vascular defect, the endovascular implant including:
         a tubular implant body; and
         a sealable circumferential collar at the tubular implant body and including:
            a variable sealing device; and
            a control lead traversing from the variable sealing device to a user and controlling variability of the variable sealing device by the user, the variable sealing device and the control lead cooperating to reversibly expand and contract the sealable circumferential collar such that the sealable circumferential collar circumferentially adjusts during deployment thereof to achieve a repositionable fluid-tight seal between the sealable circumferential collar and the internal walls of the blood vessel.

2. The sealable vascular endograft system according to claim 1, wherein:
   the tubular implant body is non-elastic; and
   the sealable circumferential collar is elastic.

3. The sealable vascular endograft system according to claim 1, wherein the sealable circumferential collar is a proximal sealable circumferential collar to be deployed proximal to the vascular defect and the tubular implant body has a distal end, and further comprising a distal sealable circumferential collar at the distal end of the tubular implant body, the distal sealable circumferential collar including a distal variable sealing device reversibly expanding and contracting the distal sealable circumferential collar to circumferentially adjust the distal sealable circumferential collar during deployment thereof to achieve a repositionable fluid-tight seal between the distal sealable circumferential collar and internal walls of the blood vessel distal to the vascular defect.

4. The sealable vascular endograft system according to claim 1, wherein the tubular implant body has a distal end, and which further comprises:
   a distal variable sealing device at the distal end of the tubular implant body; and
   a distal control lead connected to the distal variable sealing device, the distal control lead traversing the implant delivery catheter from the distal variable sealing device at least to the catheter proximal end when housed therein for interface by the user.

5. The sealable vascular endograft system according to claim 1, wherein the tubular implant body is straight.

6. The sealable vascular endograft system according to claim 1, wherein the tubular implant body branches into two or more branches.

7. The sealable vascular endograft system according to claim 1, wherein the tubular implant body is a plurality of tubular implant bodies each operable to be connected to another of the tubular implant bodies in a variably sealable manner by operation of the respective sealable circumferential collar as controlled by the respective variable sealing device to achieve a repositionable fluid-tight seal between:
   a proximal-most one of the sealable circumferential collars and the internal walls of the blood vessel proximal to the vascular defect; and
   a distal-most one of the sealable circumferential collars and the internal walls of the blood vessel distal to the vascular defect.

8. The sealable vascular endograft system according to claim 1, wherein the tubular implant body is of:
   solid construction; and
   a biocompatible material.

9. The sealable vascular endograft system according to claim 1, wherein the tubular implant body is of:
   woven construction; and
   a biocompatible material.

10. The sealable vascular endograft system according to claim 1, wherein the endovascular implant is coated with a biocompatible material.

11. The sealable vascular endograft system according to claim 1, wherein the vascular defect is an aneurysm.

12. The sealable vascular endograft system according to claim 1, wherein the endovascular implant further comprises a retraction device to reposition the endovascular implant during deployment.

13. The endovascular implant according to claim 1, further comprising a retraction device repositioning the tubular implant body during deployment.

14. A method of treating a vascular defect in a blood vessel within a patient, the method comprising:
   providing an endovascular implant with:
      a tubular implant body;
      a sealable circumferential collar at the tubular implant body and having a variable sealing device to reversibly expand and contract the sealable circumferential collar; and
      a control lead operatively connected to the variable sealing device to reversibly expand and contract the sealable circumferential collar, the control lead traversing from the variable sealing device to a user for interface by the user when the endovascular implant is at the vascular defect;
   guiding the endovascular implant in a compressed or folded state to the vascular defect;
   cooperatively manipulating the control lead and the variable sealing device to circumferentially adjust the sealable circumferential collar to achieve a fluid-tight seal between the sealable circumferential collar and the internal walls of the blood vessel adjacent the vascular defect, the manipulation of the control lead and the variable sealing device reversibly expanding and contracting the sealable circumferential collar during deployment thereof to reposition the fluid-tight seal; and
   removing the control lead from the patient.

15. The method according to claim 14, wherein the sealable circumferential collar is a proximal sealable circumferential collar, the tubular implant body has a distal end, and which further comprises:
   providing a distal sealable circumferential collar at the distal end of the tubular implant body, the distal sealable circumferential collar including a distal variable sealing device operating to reversibly expand and contract the distal sealable circumferential collar when controlled;
   operatively connecting a distal control lead to the distal variable sealing device to reversibly expand and contract the sealable circumferential collar, the distal control lead traversing from the distal variable sealing device to a user for interface by the user when the endovascular implant is at the vascular defect; and
   cooperatively manipulating the distal control lead and the distal variable sealing device to circumferentially adjust the distal sealable circumferential collar to achieve a fluid-tight distal seal between the distal sealable circumferential collar and the internal walls of the blood vessel adjacent the vascular defect, the manipulation of the distal control lead and the distal variable sealing device reversibly expanding and contracting the distal sealable circumferential collar during deployment thereof to reposition the fluid-tight distal seal.

16. The method according to claim 14, further comprising the step of connecting one or more additional endovascular implants in a variably sealable manner by operation of the sealable circumferential collars as controlled by the respective variable sealing devices and control leads to achieve a repositionable fluid-tight seal between:
   a proximal-most one of the sealable circumferential collars and the internal walls of the blood vessel proximal to the vascular defect; and
   a distal-most one of the sealable circumferential collars and the internal walls of the blood vessel distal to the vascular defect.

17. The method according to claim 14, wherein the vascular defect is an aneurysm.

* * * * *